United States Patent [19]
Armstrong et al.

[11] Patent Number: 6,096,532
[45] Date of Patent: Aug. 1, 2000

[54] PROCESSOR APPARATUS FOR USE IN A SYSTEM FOR MAINTAINING AND GROWING BIOLOGICAL CELLS

[75] Inventors: R. Douglas Armstrong, Ann Arbor; James Maluta, Dexter, both of Mich.; David W. Roecker, Denver, Colo.

[73] Assignee: Aastrom Biosciences, Inc., Ann Arbor, Mich.

[21] Appl. No.: 08/921,847

[22] Filed: Sep. 2, 1997

Related U.S. Application Data

[63] Continuation of application No. 08/483,520, Jun. 7, 1995, abandoned.

[51] Int. Cl.⁷ ..................................................... C12M 3/02
[52] U.S. Cl. ...................... 435/286.5; 435/325; 435/383; 435/284.1; 435/287.1; 435/289.1
[58] Field of Search ..................................... 435/325, 383, 435/284.1, 287.1, 289.1, 297.5, 286.5

[56] References Cited

U.S. PATENT DOCUMENTS

| | | | |
|---|---|---|---|
| 4,696,902 | 9/1987 | Bisconte | 435/300 |
| 4,812,392 | 3/1989 | Miyake et al. | 435/3 |
| 4,839,292 | 6/1989 | Cremonese | 435/313 |
| 4,894,342 | 1/1990 | Guinn et al. | 435/291 |
| 5,135,853 | 8/1992 | Dziewulski et al. | 435/41 |
| 5,316,905 | 5/1994 | Mori et al. | 435/3 |
| 5,352,414 | 10/1994 | Rothenberg | 422/101 |
| 5,424,209 | 6/1995 | Kearney | 435/284 |
| 5,459,069 | 10/1995 | Palsson et al. | 435/289.1 |

FOREIGN PATENT DOCUMENTS

| | | |
|---|---|---|
| 0 182 926 A1 | 11/1984 | European Pat. Off. ......... C12M 1/34 |
| WO 91/02049 | 2/1991 | WIPO . |
| WO 93/11498 | 6/1993 | WIPO . |
| WO 94/28501 | 12/1994 | WIPO . |

OTHER PUBLICATIONS

Edgington, Stephen M., "New Horizons for Stem–Cell Bioreactors," Bio/Technology, vol. 10, Oct., 1992, pp. 1099–1106.

Armstrong, R. Douglas et al., "Clinical Systems for the Production of Human Cells and Tissues," Bio/Technology, vol. 13, May, 1995, pp. 449–453.

"Touch the Future," Dallas Semiconductor, undated.

*Primary Examiner*—James C. Housel
*Assistant Examiner*—Jennifer Shaver
*Attorney, Agent, or Firm*—Sheppard, Mullin, Richter & Hampton LLP; James R. Brueggemann

[57] ABSTRACT

A processor apparatus is disclosed, for conditioning a portable cassette as part of a process in which biological cells contained within a sterilizable cell growth chamber of the cassette are maintained and grown ex vivo, without exposing the cells to the external environment. The processor apparatus includes a support configured to removably receive the portable cassette and to be movable in a controlled manner, and it further includes a flow control actuator engageable with a media flow path of the portable cassette, which communicates with the cell growth chamber. The processor apparatus further includes a controller that controls the flow control actuator and the support, such that a quantity of growth medium is selectively delivered to the cell growth chamber, such that the cassette is moved in a manner that properly distributes the biological cells throughout the chamber, and such that biological cells are harvested from the cell growth chamber, all without exposing the chamber and the media flow path to the external environment. The processor apparatus also may be configured to retrieve data from, and to store data to, an updatable memory device carried on the portable cassette.

13 Claims, 9 Drawing Sheets

PROCESSOR APPARATUS FOR USE IN A SYSTEM FOR MAINTAINING AND GROWING BIOLOGICAL CELLS

This application is a continuation of application Ser. No. 08,483,520 filed Jun. 7, 1995, now abandoned.

BACKGROUND OF THE INVENTION

1. Introduction

This invention relates generally to apparatus for maintaining and growing biological cells ex vivo and, more particularly, to apparatus of this kind that maintains and grows the cells in a portable cassette while maintaining a sterile system that is closed to the external environment.

Many medical disorders can now be resolved by using transplanted cells, tissues, or organs. Transplantation has evolved from the surgical transfer of tissue from one part of a patient's body to another, to the surgical transfer of organs and tissues between individuals, to the transplantation of blood and immune systems between individuals. With increased demonstration of the medical benefit of tissue transplantation, the demand for organs and tissues suitable for these procedures has far exceeded the availability. Furthermore, in those cases where availability is less an issue, e.g., bone marrow, the procedure is cost prohibitive and can be invasive for the donor or the patient.

As an evolution of the clinical need, two related fields have evolved, which have been termed "cell therapy" and "tissue engineering." Cell therapy generally refers to the use of living cells, rather than drugs, to treat a clinical disorder or disease. Perhaps the most widely practiced form of cell therapy today is with bone marrow or hematopoietic stem cell transplantation in patients who have received hematopoietic toxic chemotherapy or radiation. This procedure involves the reinfusion of early stage cells that originate in the bone marrow, so that these cells can reestablish a patient's blood and immune system, and often the bone marrow tissue as well. Through this cell therapy process, the hematopoietic toxicity from cancer treatment is remedied.

Tissue engineering generally refers to the utilization of different disciplines between engineering, physiology, and cell biology, to develop at least a partially living tissue that is capable of normal tissue function. Once produced, this tissue may be transplanted into humans to restore or improve normal tissue or organ function. Numerous biotechnology companies are engaged in projects to engineer human tissues for transplantation.

For both cell therapy and tissue engineering procedures, there is a critical need to be able to process and/or produce ex vivo the cells that will be used for the therapeutic transplant. Biological science has now progressed such that, for many of the human tissues, methodology has been developed so that the key cells of that tissue can be grown outside the body. As a result, a clinically useful amount of tissue can be generated from a small amount of starting material, which is obtained with a minimally invasive technique. With this achievement, the opportunity for increasing and more diverse use of tissue transplantation is offered.

In parallel with this advancement, and largely dependent upon its success, are the numerous gene therapy approaches being advanced to initial clinical trials that involve the ex vivo genetic manipulation of cells and tissue. Gene therapy involves transduction of the genome of the cell to achieve correction of a defective gene, regulation of a disease condition, or production of a beneficial molecule. Those gene therapy procedures that will benefit from ex vivo administration of a gene vector to an expanded or donor tissue in order to enhance the targeting of the gene and avoid this systemic administration (likely to include most conceivable gene therapies for the next decade or longer) will be well served by the above advancements in tissue genesis and production.

The particular physical and biological requirements for the production of cells and tissues of blood, skin, cartilage, bone, pancreas, the nervous system, and various other endothelial and mesenchymal tissues of interest to cell and genetic therapists, will vary. However, two key components are necessary in order to grow cells and tissues ex vivo: 1) cells of self or donor origin that are capable of replicating and differentiating, as needed, for the formation of functioning tissue; and 2) an ex vivo system comprised of biocompatible materials that provide for the physiological requirements (e.g., surface attachment, medium exchange, and oxygenation) for the above cells to grow.

An excellent example of the merging interface of cell therapy with tissue engineering is the ex vivo production of human bone marrow. This process illustrates as well the interrelationship between the cell/tissue production methodology and the medical device requirements to properly implement the tissue production.

Although lacking the physical geometry that is a feature of other tissues or organs, bone marrow is a tissue comprised of many different cell types, ranging from different stromal fibroblasts, mesenchymal cells, to stem cells and the other cells of the hematopoietic system. The ex vivo process found to be needed for ex vivo bone marrow growth, was to mimic the natural functional environment of the bone marrow, providing for the controlled nutrient perfusion and oxygenation of the stem and stromal cell components under precise conditions of temperature and medium composition. Key to the success was to provide culture conditions that were concurrently amenable for each of the many different cell types that are found in human bone marrow.

Using this approach of tissue engineering, for the first time, the human stem cells that are found in the bone marrow were able to not only survive in culture, but also replicate to produce more stem as well as more mature progenitor cells. This result is in direct contrast to when hematopoietic stem/progenitor cells have been isolated (e.g., CD-34 selection) prior to the culture process. In this case the stem cells do not grow and the cultures die off over a short period, presumably because heterogeneous tissue interactions have been eliminated.

With the successful production of these bone marrow tissue cells, they can be available to be used as a substitute for bone marrow transplantation. This example is an excellent demonstration of how the lost function of a damaged or destroyed tissue, e.g., bone marrow, can be repaired or restored with ex vivo engineered tissue-specific cells.

Once the basic cell/tissue production process is identified, the next requirement for therapeutic utilization is the need for clinical systems to implement the process. These systems should be amenable for routine use by the thousands of hospitals and clinics in the developed and developing world that serve the patients intended to benefit from the transplantation cells and tissues in native or genetically altered form.

2. Critical Requirements for an Ex-Vivo Cell Production Process

Cell and organ transplantation therapy to date has relied on the clinical facility to be able to handle and process cells or tissues through the use of laboratory products and processes, governed to varying degrees by standard operating procedures, and with varying FDA and other regulatory authority involvement. The procedures to date, however, generally have not required extensive manipulation of the cells or tissue beyond providing standard incubation solutions, short term storage or containment, or—as in the case of bone marrow or peripheral blood stem cells for stem cell transplants—cryopreservation. With the addition of steps that require the actual growth and production of cells or tissues for transplantation, there are many considerations that need to be addressed in order for a reliable and clinically safe process to result. This issue is the same regardless of whether the cell production is occurring at the patient care location (as might be the case for the production of cells for a stem cell transplant), or at some distant manufacturing site (as might be the case for the production of a biosynthetic device).

A. Process Reliability for an Ex Vivo Cell Production Process

Perhaps the most critical of all issues to be addressed is the technical art that is inherent with most cell culture processes. Site-to-site differences in cell culture are often sensitive. For an acceptable clinical cell culture process, the technical art or sophistication must be eliminated such that the cell product will be the same when the process is used in different physical locations.

This problem can best be handled by implementing a well characterized, robust process with automation. While the variable human factor is eliminated from the technical process, human oversight should be maintained for the quality monitoring and control process. Alternatively, highly controlled training and standard procedures can be used to address inherent variability in the practice of cell production processes as well, and in certain cases will be required when the technical steps cannot be automated.

However, if a controlled process can lead to the same result repeatedly, then it can and should be automated. From a strategic point of view, automation via a medical device is desirable because it eliminates variability due to human error or human initiative, it reduces the need for highly skilled labor and thus cost of the process, and it makes the process amenable for widespread practice. Ultimately, any manual process remains vulnerable to an ineffective automation strategy. Automation also meets a general desire by clinicians to provide better quality assurance to their patients.

B. Process Sterility—Closed Systems

With any cell culture procedure, a major concern is sterility. When the product cells are to be transplanted into patients—often at a time when the patient is immunocomprised, as is the case with stem cell transplants and with organ transplants—absence of microorganisms is mandated. Most laboratory cell culture procedures are carried out under aseptic conditions with the technician practicing so-called sterile technique. Many of the bioreactor systems that have been developed offer advantages over the manual processes in that once the culture is initiated, the culture chamber and the fluid pathway is maintained in a sterile, closed environment. However, even with these systems, the initial setup and takedown steps, such as the medium priming and collection of the cells at the completion of the process, requires non-sterile manual procedures.

Accordingly, laboratory cell culture systems are only partly closed, i.e., they involve numerous aseptic connections, are mostly operated in a controlled-environment hood, and have pre- and post-processing steps requiring open centrifuge tubes and the like. The most optimal objective is to have the culture process be carried out in a system where the culture chamber and fluid path is functionally closed to the external environment, with the sterile integrity maintained from the time the device is manufactured until it has been disposed of.

C. Cell Recovery

For cell therapy, the product of the cell culture process is the cells. Accordingly, efficient collection of the cells at the completion of the culture process is an important feature of an effective cell culture system. Recovery of cells from most cell production processes is a challenge. They are either: 1) packed into the interstices of a make-do dialysis cartridge, or 2) suspended in many liters of culture medium. The first case necessitates unreasonable physical force to dislodge cells (being neither reliable nor easily automated), and the second case requires significant time, patience, and a certain degree of good fortune (being neither reliable nor closed).

The better approach for production of cells as the product is to culture cells in a defined, reasonable space, without physical barriers to recovery, so that simple elution of product results in a manageable, concentrated volume of cells amenable to final washing in a commercial, closed system cell washer designed for the purpose. An ideal system would allow for the efficient and complete removal of all cells produced, including both adherent and nonadherent cells. Furthermore, the harvest process should be able to be completed without breaking the sterile barrier of the fluid path of the culture chamber.

D. Optimization of Key Culture Parameters by Design

With any large volume cell culture, several fundamental parameters require almost constant control. Cultures must be provided with the medium that allows for normal metabolic functions and growth, and typically this medium is delivered to the cell by a pumping mechanism (e.g., in a bioreactor) or by a technician manually feeding or exchanging the medium on a regular basis. As an additional part of this exchange process, culture byproducts are also removed from the culture.

Growing cells or tissue also requires a source of oxygen. Different cell types have different oxygen requirements, and all cell cultures have differing oxygen delivery requirements depending on the density of the culture. Accordingly, a controllable and flexible means for providing oxygen to the cells is a necessary component of the culture system.

Even distribution of the cell population and medium supply in the culture chamber is an important process control. This control is often achieved by use of a suspension culture design, which can be effective where cell-to-cell interactions are not as important as cell-to-medium interactions. Examples of suspension culture systems include various tank reactor designs and gas-permeable plastic bags. Aside from mature blood cells, such as T-cells, such designs are often deleterious as they impede the development of three dimensional structure in tissue. The growth of bone marrow stem cells is precluded in environments favoring single cell suspensions, because stem cells appear to desire contact with stromal and other accessory cells in order to replicate.

E. Status Feedback and Production Record Capability

The essence of "good manufacturing practice" is: 1) equipment and facilities that are capable of reliably providing the desired product, 2) process control that through validation demonstrate an ability to produce product within desired specifications, and 3) final product and process documentation controls that prevent mix-ups or inappropriate release of product before complete review of test and production records is conducted and accepted.

In a purely manual manufacturing environment, this is accomplished by selecting well-qualified personnel, providing them with extensive training, and developing a system of standard operating procedures and extensive documentation that provides for quality assurance. In an automated manufacturing environment, the principles of process validation are used to demonstrate that the process is stable and capable of meeting specifications. The principles of statistical process control are then implemented to monitor the process to assure consistent conformance to specifications.

In today's environment, as cell culture becomes prominent in clinical care, much of the process control and record keeping will depend upon trained operators, maintaining detailed records. The future lies in the availability of equipment and materials that are designed and manufactured for the intended purpose and automation that allows the process to be validated and controlled. Only under these conditions can cellular therapy be delivered cost effectively to the market.

3. Cell Culture Devices and Procedures

In nature, tissue function and viability depends upon the life support process that is mediated by the vascular system. Nutrients, physiological salts, and oxygen are all brought to the tissue through arteries. The waste products produced by the tissue, which can often be toxic to the tissue, are carried away by the veins. The other major component of tissue maintenance and repair is cellular—the pool of progenitor or stem cells that can replace cells lost or damaged.

Accordingly, for tissue to be developed ex vivo, these same elements are required to be managed by the culture devices and procedures. In other words, the stem/progenitor cells needed to expand the cellular component of the tissue must be maintained in a physical and biological environment that is biocompatible and provides a means to control delivery of nutrients and oxygen to the cells, and carry away waste or other byproducts of the growing cell populations.

A. Traditional Cell Culture Processes

Over the past decade, increasing numbers of medical researchers have sought to develop treatments based in part on the culture of human blood cells, including lymphocytes, monocytes, neutrophil precursors, and immature blood cells including stem and progenitor cells. The evolution of technologies adapted or developed to meet these needs provides an excellent demonstration of the need for clinical systems for the production of human cells for therapy.

1. Laboratory Environment

Traditional cell culture technologies depend upon controlled environments for cell handling. Cell culture laboratories incorporate such features as laminar flow hoods controlled access to the laboratory by gowned personnel, and regular sterilization procedures to decontaminate laboratory surfaces. Personnel require extensive training to practice sterile technique, to avoid contamination of open containers and cell transfer devices by contact with non-sterile materials. In spite of these prophylactic measures, outbreaks of contamination in traditional cell culture laboratories, e.g., fungus contamination, is a common occurrence, often with the impact of halting operations for days or weeks while the source of the contamination is determined and resolved.

Traditional cell culture technologies further depend upon incubation in an environment providing controlled gas mixtures and controlled temperature, usually satisfied by the use of commercial incubators ranging in size from large benchtop units to large floor-standing units.

Therapeutic requirements for numbers of blood cells (typically 10 to 100 billion per patient treatment) and limitations in maximum cell culture density (typically one billion per liter of medium), together with space requirements for major laboratory hardware (e.g., hoods, incubators, refrigerators) and personnel activity, have resulted in considerable laboratory space requirements per patient therapy. Laboratory support operations, including preparation of media and the practice of various assays expand these space requirements and associated capital investments and labor costs. Use of traditional cell culture technology for patient therapy thus results in relatively high costs per patient treatment.

Such a laboratory environment is not conducive to the reliable and routine production of large numbers of cells for patient therapy, given its reliance on manual, highly skilled technique. Achieving "good manufacturing practices" in such an environment is a daunting challenge, requiring the development and adherence to massive volumes of standard operating procedures to eliminate inherent variability in laboratory practices.

2. Tissue Culture Flasks and Roller Bottles

The earliest cell cultures were achieved in glass petri dishes, which were largely supplanted by pre-sterilized plastic tissue culture flasks in the 1960's and 1970's. Early attempts at large scale culture of human cells for therapy in the mid-1980's involved the use of numerous glass roller bottles in a room-sized mechanized facility. Even today, most cell therapies have their genesis in plastic tissue culture flasks, and process scale-up involves use of more, larger so-called T-flasks, which are fed manually in a laminar flow hood.

Manufacturers of tissue culture media used in human therapy have gradually moved away from glass bottle packaging to plastic bottles, and most recently have been developing flexible plastic container systems for their media, similar to those used for decades for intravenous (IV) solutions. The use of flexible containers has been driven in part by the desire by a few customers to eliminate open transfer steps for culture media, which can introduce potential contamination.

As described earlier, one preferred objective is to provide a culture process that can deliver medium and oxygenation at uniform and controlled rates that mimic serum perfusion of tissue in vivo. In order to achieve these relatively slow delivery rates, a means of internally oxygenating the cells is often required. This is one requirement that is ideally met using the simplest of cell culture processes—a culture dish. Here the surface of the culture is uniformly exposed to oxygen, and oxygen is available to the cells as needed. A similar situation can be produced in a flatbed bioreactor, with a gas permeable/liquid impermeable membrane a short distance from the cell bed. This allows for a system to have variable medium perfusion rates from stagnant to high, with the oxygenation of the culture remaining constant and uniform.

3. Flexible Tissue Culture Containers

Flexible tissue culture containers, or culture bags, were developed in the mid-1980's, in response to clinicians' desire to perform culture of cells for human therapy in a reproducible and reliable manner across multiple laboratories and institutions. The use of aseptic tubing connections technology, used commonly in the medical device industry (e.g., for blood collection and transfusion containers), rather than conventional sterile technique in laminar flow hoods, reduces the probability of contamination to less than one chance in a thousand per connection. Flexible containers fitted with aseptic connectors were appropriated from blood banking, where blood platelet concentrates were stored for several days in incubators in gas-permeable, liquid-impermeable plastic containers, which permitted bicarbonate pH buffering of the platelets by the carbon dioxide gas in the incubator.

In the late 1980's, extensive trials of various forms of lymphocyte therapy were conducted using such culture bags, with low incidence of contamination. Today, these culture containers continue to find use in experimental cell therapies where oxygen consumption requirements are minimal and non-adherent cells grow satisfactorily in suspension culture. Such containers do not, however, support the growth of human stem cells that require contact with a heterogeneous population of adherent stromal cells. Advantages of culture bags include relative simplicity of use, reduce skill level requirements, and potential use without laminar flow hoods. However, to date, processes utilizing culture bags remain labor- and space-intensive and are limited in their clinical applicability.

4. Bioreactors

Platform-operated culture systems, typically referred to as bioreactors, have been available commercially for many years and employ a variety of types of culture technologies. Of the different bioreactors used for mammalian cell culture, most have been designed to allow for the production of high density cultures of a single cell type. Typical application of these high density systems is to produce as the end-product, a conditioned medium produced by the cells. This is the case, for example, with hybridoma production of monoclonal antibodies and with packaging cell lines for viral vector production. These applications differ from applications where therapeutic end-product is the harvested cells themselves.

These systems have made an important first step towards a usable clinical system. Once set up and running, the systems provide automatically regulated (not necessarily uniform) medium flow, oxygen delivery, and temperature and pH controls, and they allow for production of large numbers of cells. While bioreactors thus provide some economies of labor and minimization of the potential for mid-process contamination, the set-up and harvest procedures involve considerable labor requirements and open processing steps, which require laminar flow hood operation (some bioreactors are sold as large benchtop environmental containment chambers to house the various individual components that must be manually assembled and primed). Further, such bioreactors are optimally designed for use with a homogeneous cell mixture, and not the mixture of cell types that exists with tissues such as bone marrow.

Many bioreactors have a high medium flow rate requirement for operation. The reason of this feature is that the oxygenation mechanism is to oxygenate the medium outside of the growth chamber, immediately before the medium is perfused into the growth chamber. Since a high density culture will quickly deplete the medium of oxygen, the medium must have a short residence time in the chamber, in order to be reoxygenated and recirculated back into the culture chamber. Furthermore, this process results in an absence of uniformity in oxygenation of the growing tissue, since cells proximal to the medium inlet see much higher concentrations of oxygen than do the cells proximal to the medium outlet. This results in the different cells growing in different areas of the bioreactor.

An additional limitation is that many of the bioreactor designs, such as the various three-dimensional matrix-based designs (e.g., hollow fiber cartridges or porous ceramics), can impede the successful recovery of expanded cells and/or tissues, particularly when culture growth is vigorous, and also can limit mid-procedure access to cells for purposes of process monitoring.

The various trade-offs described have limited the utility of these systems and, in general, such bioreactors have not been used for human cell therapy as much as the less automated but often more user-friendly culture bag systems.

It should, therefore, be appreciated that there is a need for a cell production system that can maintain and grow selected biological cells without being subject to the foregoing deficiencies. There is a particular need for such a system that can receive, maintain and grow such cells in a sterile system within a portable cassette without exposing that sterile system to the external environment. The present invention fulfills that need.

SUMMARY OF THE INVENTION

The present invention is embodied in an apparatus, and its components and related methods, that receives, maintains and grows biological cells ex vivo within a portable cassette, without exposing the cells to the external environment. The portable cassette includes a cell growth chamber within which the cells are maintained and grown, a media container configured to carry a quantity of a suitable growth medium, and a waste container configured to carry growth media discharged from the cell growth chamber. These elements are connected together to form a sterile system that is closed to external environment. The closed, sterile system also can incorporate a harvest container configured to carry growth media and biological cells discharged from the cell growth chamber.

In addition to the portable cassette, the apparatus further includes a plurality of instruments, each configured to receive and condition the portable cassette during a different stage of the cell growth process. The cassette is conveniently transportable from each instrument to the next, as the cell growth process progresses. One such instrument is a processor configured for use in priming the cassette's cell growth chamber with growth media and in mixing biological cells with that growth media and distributing the cells, e.g., uniformly, throughout the cell growth chamber. A second such instrument is an incubator configured to condition the cassette while the biological cells are being maintained and grown. The processor instrument also is configured for use in harvesting the biological cells after the incubation stage.

More particularly, the processor apparatus includes a support such as a platform configured to removably receive the portable cassette and further configured to be movable in a controlled manner. A flow control actuator is engageable with a media flow path of the portable cassette when the cassette is received by the support, and a controller controls the flow control actuator such that a determined quantity of the growth medium is delivered from the media container to the cell growth chamber of the portable cassette. In addition, the controller thereafter controllably moves the support in a predetermined manner, such that the biological cells are distributed substantially uniformly throughout the cell growth chamber. The portable cassette further includes a flow control device engageable with the media flow path, and the flow control actuator of the processor apparatus is engageable with that flow control device so as to control the delivery of growth media to the cell growth chamber. The controller includes a media flow sensor that senses the delivery of growth media to the cell growth chamber and generates a corresponding detection signal, and the controller further is configured to control the flow control device so as to regulate, e.g., terminate, the delivery of growth media.

The portable cassette can further include an inoculation port through which a quantity of biological cells can be delivered to the cell growth chamber. In addition, the processor controller is configured to control the flow control actuator, after the inoculation of cells into the cell growth chamber, such that the delivery of growth media to the chamber terminates with a gas bubble remaining within the chamber. In addition, the processor controller is configured to then controllably move the support such that the gas bubble moves within the cell growth chamber in a predetermined manner, to mix the biological cells substantially uniformly with the growth media within the chamber. After that mixing has been completed, the processor controller controls the flow control actuator such that sufficient additional growth media is delivered to the cell growth chamber to substantially displace the gas bubble.

In other features of the invention, the portable cassette includes two separate casings, including a first casing that defines the cell growth chamber and a second casing that defines the growth media container. The incubator apparatus includes a first receptacle sized and configured to removably receive the first casing, and a second receptacle sized and configured to removably receive the second casing. In addition, first and second temperature regulators regulate the temperatures of the first and second receptacles to prescribed temperatures, and an interface is provided for engaging the portable cassette when the first and second casings are received in their respective receptacles, the interface being configured to control the delivery of growth media from the media container to the cell growth chamber and to control the delivery of gas from a gas supply to the cell growth chamber. This provides the appropriate conditions for the biological cells to be maintained and grown within the cell growth chamber.

The portable cassette includes a media flow path, e.g., plastic tubes and related connectors, in fluid communication with the cell growth chamber, e.g., between the chamber and the media container or between the chamber and the waste container. Engaging this media flow path, and forming part of the portable cassette, is a flow control device, which is configured to be engageable with a flow control actuator of a separate instrument, e.g., the processor apparatus or the incubator apparatus, and thereby control the flow of growth media through the cell growth chamber. The flow control device can include a plunger that is spring-biased to constrict the media flow path and a plate that is operatively connected the plunger such that, when the plate is depressed, the plunger releases its constriction of the flow path. This constriction device conveniently can be mounted on the portable cassette with the plate flush with a rear panel of the first casing.

The interface of the incubator apparatus includes an actuator engageable with flow control device when the first casing of the portable cassette is received in the first receptacle, and the actuator is controlled so as to deliver the growth media from the media container through the cell growth chamber to the waste container at a prescribed flow rate. The interface further includes a sensor that monitors the flow rate of growth media being transported through the chamber.

In another feature of the invention, the processor apparatus further is configured to condition the portable cassette so as to harvest biological cells that have been maintained within its cell growth chamber. This is achieved by initially controllably tilting the platform on which the cassette is received, while at the same time controlling one or more of various flow control devices, so that growth media and biological cells within the chamber are discharged to the harvest container via the harvest port. Thereafter, the processor apparatus controllably delivers a succession of reagents to the cell growth chamber, to dislodge additional cells from the cell bed and to deliver those dislodged cells to the harvest container, again via the harvest port.

In a separate feature of the invention, the portable cassette includes a memory device that stores information about the portable cassette and its event history, the biological cells and growth media that are carried by the cassette, and process instructions for the apparatus with which the cassette is configured to be used. The interfaces of both the processor apparatus and the incubator apparatus preliminarily retrieve information from this memory device and thereafter controllably condition the cassette according to the retrieved information. In addition, the interfaces are configured to update the memory device with information pertinent to the condition of the portable cassette during the time it is received by respective apparatus. The memory device conveniently can be carried on the rear panel of the portable cassette's first casing.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENT

Figure 1:
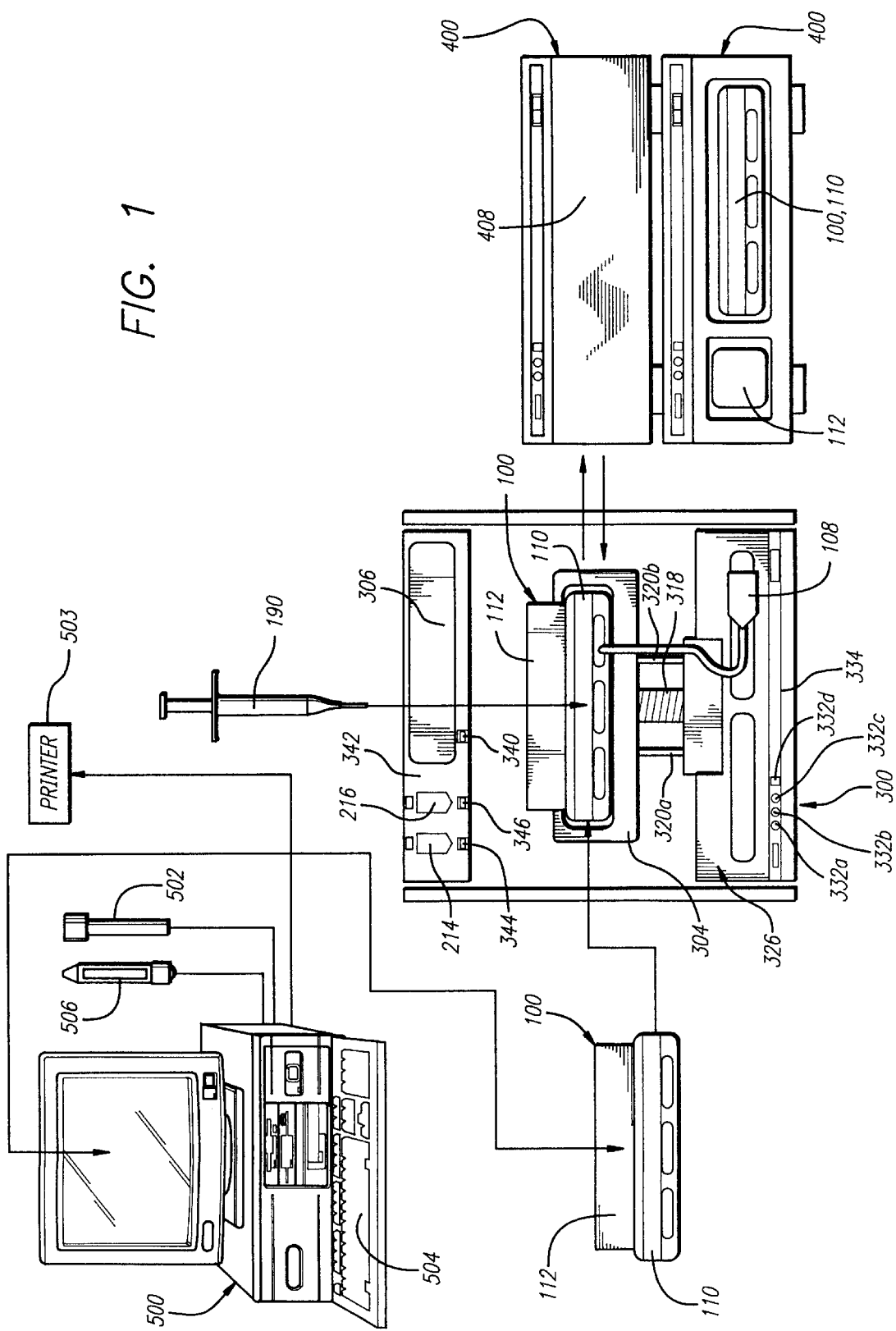
FIG. 1 is schematic diagram of a cell production system in accordance with the invention, including a portable cassette having a cell growth chamber, a processor instrument used to distribute inoculated biological cells within the cell growth chamber and later used to harvest the cells that have been maintained and grown, an incubator instrument for incubating the portable cassette such that the cells are maintained and grown, and a system manager.
Figure 2:
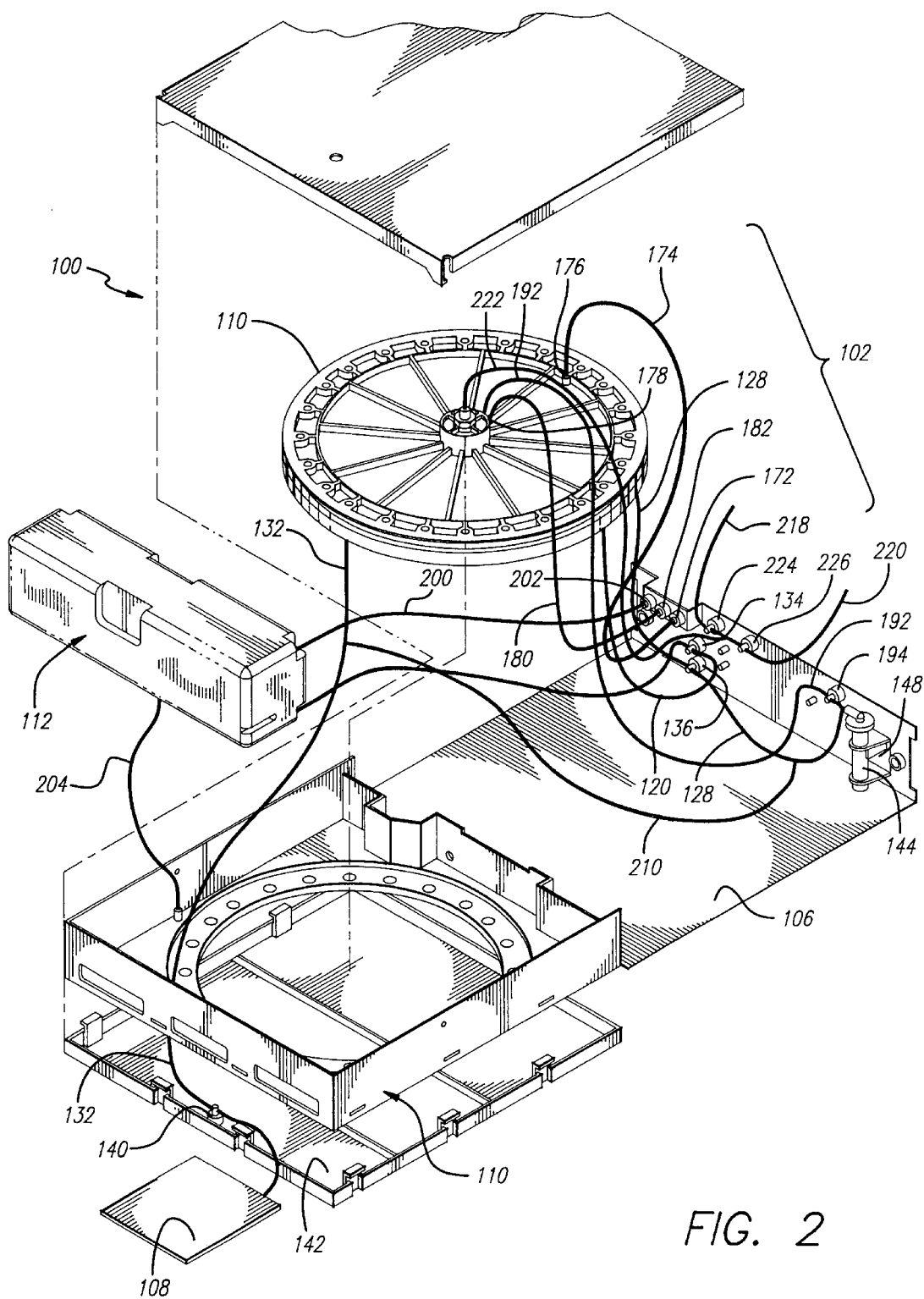
FIG. 2 is an exploded perspective view of the portable cassette of FIG. 1.

With reference now to the drawings, and particularly to FIGS. 1 and 2, there is shown a cell production system embodying the invention, for ex vivo maintaining and growing biological cells such as human stem cells and hematopoietic progenitor cells. The cells are grown from a small starting cell population, and, in the case of hematopoietic progenitor cells, a sufficient volume of cells can be grown and harvested to complete a bone marrow transplantation or a nadir prevention/rescue resulting from therapies such as high dose chemotherapy or radiation. The cell production system of FIG. 1 includes: 1) a disposable portable cassette (three cassettes 100A, 100B and 100C are depicted) having a cell growth chamber (FIG. 2) in which the expansion and growth of the cells occurs, 2) a processor instrument 300 that is used initially to prime and inoculate the portable cassette and later to harvest cells from the cassette, 3) an incubator instrument (two incubator instruments 400A and 400B are depicted) that is used to control biological and physical environment of the cell cassette while the cell expansion and growth is occurring, and 4) a system manager 500 that provides an operator interface, for monitoring the cell growth occurring simultaneously in as many as 50 separate portable cassettes.

As mentioned above, three separate portable cassettes are shown in FIG. 1. A first cassette 100A is shown by itself at the left of the drawing, a second cassette 100B is shown received by the processor instrument 300, and a third cassette 100C is shown received by the incubator instrument 400. Also as mentioned above, two separate incubator instruments are shown, one stacked above the other. The upper incubator instrument 400A is shown with its front door closed, and the lower incubator instrument 400B is shown with its front door removed, to reveal the instrument's reception of a portable cassette.

As shown in FIG. 2, the portable cassette 100 includes, in addition to the cell growth chamber 102, a growth media container 104, a waste container 106, and a harvest bag 108, all of which are connected together to form a system that is closed to the external environment. The media container is initially charged with an appropriate growth medium required for the cell culture, and it can include specified growth factors and glutamine. This system can be sterilized, as by irradiation, during the cassette's initial assembly. The processor instrument 300 (FIG. 1) and the incubator instrument 400 both are configured to condition the portable cassette during separate stages of the cell growth process, without disturbing the cassette's closed, sterile system. Biological cells thereby can be received, maintained and grown by the system without the need for highly trained laboratory personnel or special environmental equipment such as a laminar flow hood, but with minimal risk of contamination.

Figure 3:
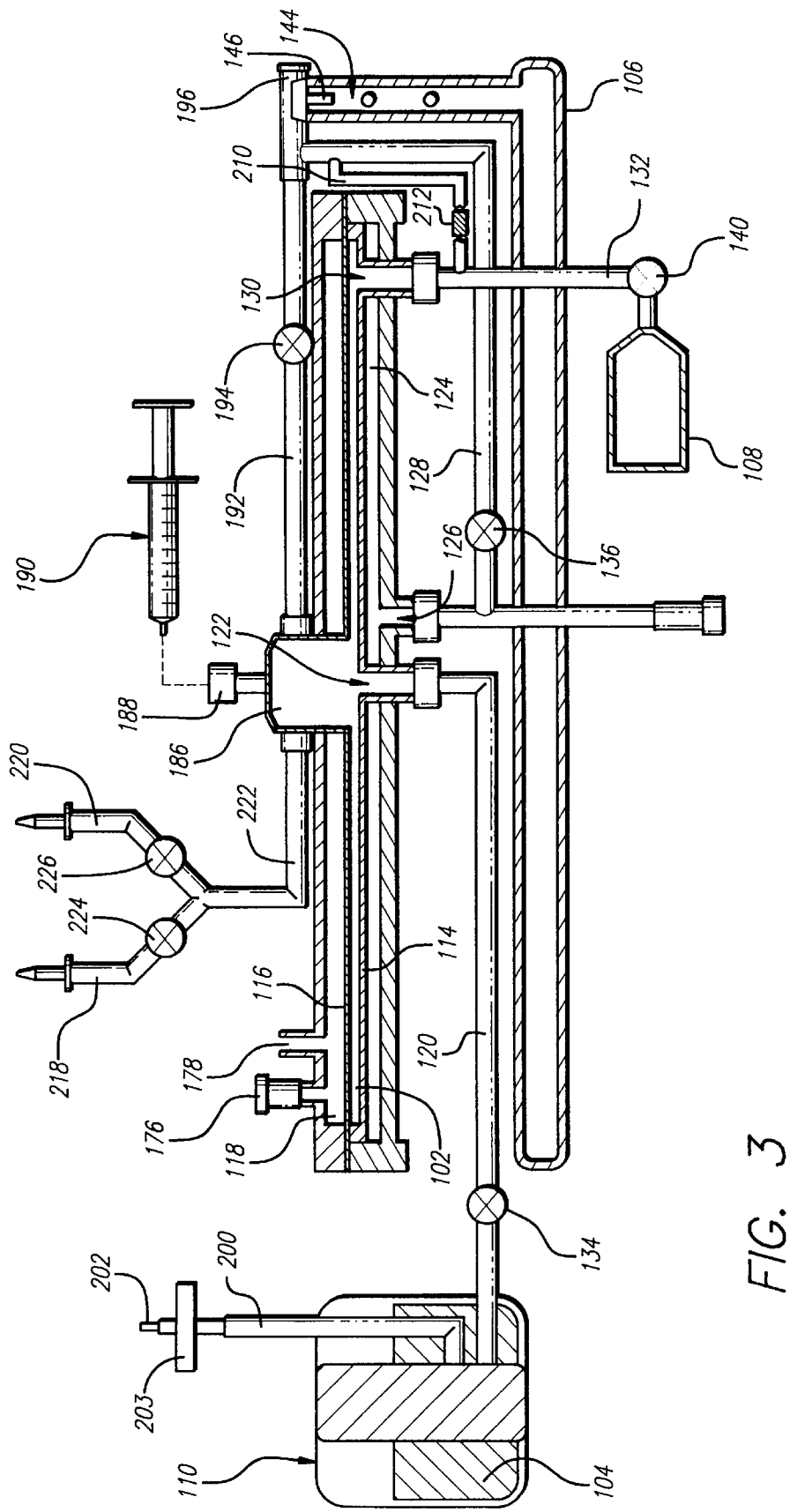
FIG. 3 is a schematic diagram showing the interconnections between the cell growth chamber, the media container, the waste bag, the harvest bag, and the harvest reagent containers of the portable cassette of FIG. 2.

More particularly, and with reference to FIG. 2, the portable cassette 100 includes a main casing 110 that houses the cell growth chamber 102, the waste container 106, and the harvest bag 108, and further includes a supplementary casing 112 that houses the growth media container 104 (FIG. 3). As shown in FIG. 3, the cell growth chamber, in the preferred embodiment, is a shallow cylinder defined by a planar, disk-shaped, plastic cell bed 114 and an adjacent, closely spaced, gas-permeable/liquid-impermeable membrane 116. In use, biological cells are distributed substantially uniformly over the cell bed, where they are nourished by growth media that is pumped radially outwardly through the chamber at a selected flow rate. Oxygen and other prescribed gases, selected for pH stability, are supplied to the cells through the membrane 116, from a shallow, cylindrical gas chamber 118 located on the side of the membrane opposite the cell growth chamber.

Figure 4:
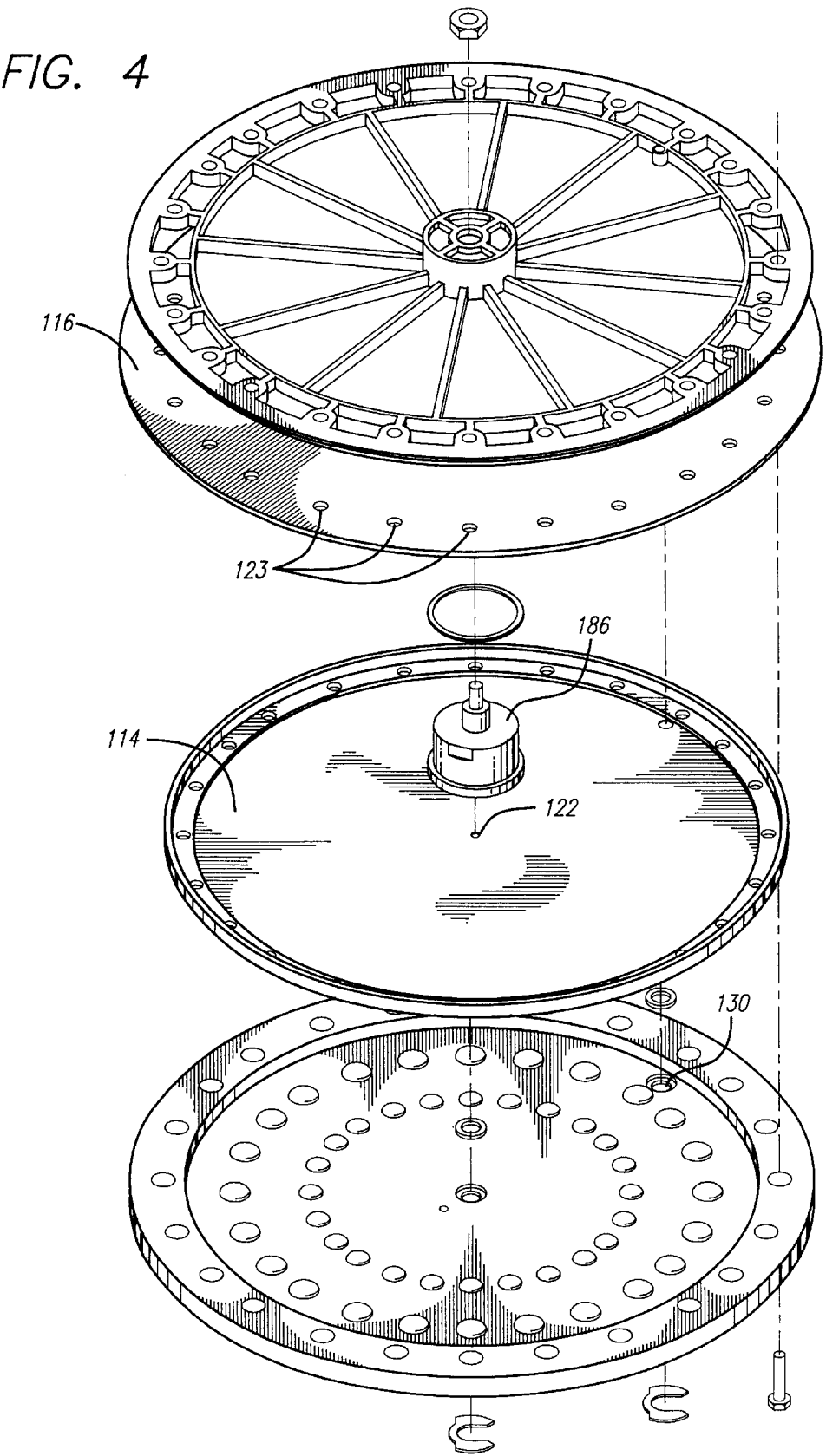
FIG. 4 is an exploded perspective view of the cell growth chamber of the portable cassette of FIG. 2.

With continued reference to FIGS. 2 and 3, the growth media is delivered to the cell growth chamber 102 from the media container 104 via a media supply tube 120 and a supply port 122 located in the center of the chamber's cell bed 114. Waste media is delivered from the cell growth chamber to the waste container 106 via, in order, 1) a plurality of ports 123 (FIG. 4) spaced uniformly around the periphery of the cell bed 114, 2) a shallow, cylindrical waste reservoir 124 located beneath the cell growth chamber, on the opposite side of the cell bed, 3) a waste port 126 located near the center of that waste reservoir, and 4) a waste tube 128. Further, the biological cells that have been nourished and grown in the cell growth chamber 102 are transferred to the harvest bag 108 via a harvest port 130 located in the cell bed, adjacent to the chamber's periphery, and a harvest tube 132.

The media supply tube 120 and the waste tube 128 pass through spring-biased valves 134 and 136, respectively, mounted on a rear panel 138 of the main casing 110. The harvest tube 132 passes through a similar spring-biased valve 140 mounted on a bottom wall 142 of the main casing. These valves are appropriately controlled by the processor instrument 300 and by the incubator instrument 400 during their separate stages of the cell growth process.

A portion of the waste tube 128 is configured as a drip chamber 144, for use in measuring the flow rate of growth media moving through the tube, and thus through the cell growth chamber 102. The drip chamber includes a drip nozzle 146 that delivers the growth media in individual droplets, and this chamber is located adjacent to an aperture 148 in the rear panel 138 of the main casing 110. Drip detectors 302 and 402 located in the respective processor instrument 300 and incubator instrument 400 are positioned and configured to automatically detect media droplets passing through the drip chamber when the corresponding instrument has received, and is conditioning, the portable cassette 100.

Figure 6:
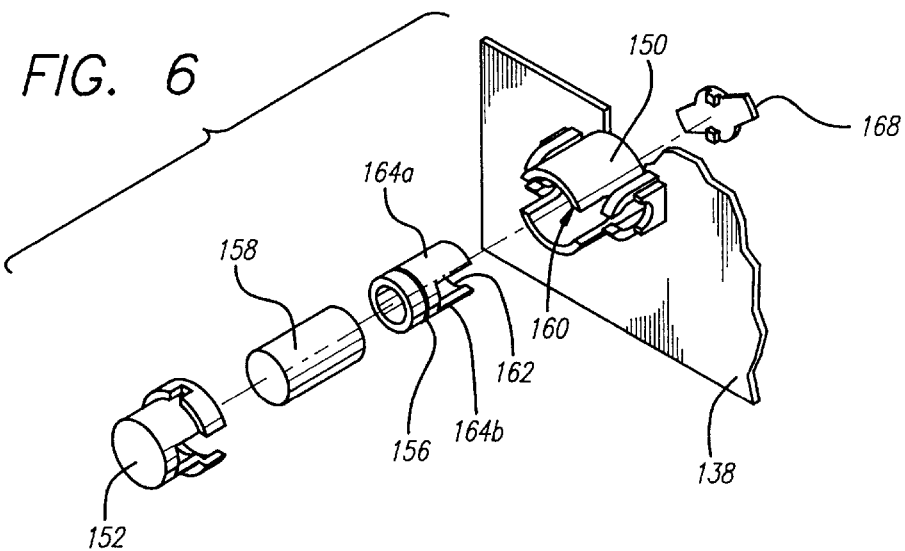
FIG. 6 is an exploded perspective view of one of several identical fluid control valves included in the portable cassette of FIG. 2.

FIG. 6 is an exploded perspective view of the spring-biased media supply valve 134, which is used to control the flow of growth media through the supply tube 120, from the media container 104 to the cell growth chamber 102. This valve is identical in structure to the waste valve 136 and the harvest valve 140. The depicted valve includes a generally cylindrical base 150 that is secured to the inner side of the main casing's rear panel 138, aligned with a circular aperture (not visible in the drawing) formed in the panel. A cap 152 is attached to the inner end of the base, to define a central recess in which are located a plunger 156 and a compression spring 158 that biases the plunger toward the base.

The facing surfaces of the base 150 and the spring-biased plunger 156 are configured as generally pyramidal anvils 160 and 162, respectively, and the media supply tube 120 is positioned between, and thereby constricted by, the two anvils. The plunger includes a pair of legs 164a and 164b that extend through slots (not shown) in the base and into the aperture in the rear panel 138. A generally circular actuation plate 168 is secured to the legs, and, when the valve is assembled, this plate lies substantially flush with the rear panel. A space is defined beneath the actuation plate, to accommodate movement of the plate toward of the base, against the yielding bias of the compression spring 158. Thus, a sufficient pressure applied to the actuation plate will overcome the spring bias and move the plunger's anvil 162 away from the base's anvil 160, thereby removing the constriction of the media supply tube 120 and allowing growth media to flow through it.

With reference again to FIGS. 2, 3 and 5, oxygen and other prescribed gases are delivered to the portable cassette 100 via a gas-in connection 172 located on the rear panel 138 of the main casing 110, and from there are delivered to the gas chamber 118 via a gas-in line 174 and a gas-in port 176. Waste gases are discharged from the gas chamber via a gas-out port 178 and gas-out line 180 to a gas-out connection 182 located on that same rear panel. These gas-in and gas-out connections are accessed by the incubator instrument 400 during the incubation stage of the cell growth process. The gas-in connection includes a sterile barrier filter 183 to ensure that the gas delivered to the gas chamber remains sterile. The gas chamber preferably takes the form of a concentric circle labyrinth, with the gas-in port located at one end of the labyrinth and the gas-out port located at the other end.

The cell growth chamber 102 includes an enlarged center cavity 186 extending above its center portion, which serves several important functions, as will be described below. One such function is to provide space within the chamber to allow the inoculation of biological cells through a septum 188, using a syringe 190. A vent, or center cavity, tube 192 extends from this center cavity through a spring-biased valve 194 to a sterile vent 196. This valve is mounted on the rear panel 138 of the main casing 110, and it has the same structure as the media supply valve 134, described above.

As mentioned above, the growth media container 104 is housed within the supplementary casing 112. The media supply tube 120, which extends from the media container to the cell growth chamber 102, thus extends from the supplementary casing to the main casing 110. The growth media container preferably has a rigid body, and the growth media it contains is pressurized by an air supply line 200, which extends from the supplementary casing to the main casing and terminates at an air supply port 202 mounted on the main casing's rear panel 138. A sterile barrier filter 203 ensures that the pressurized air that reaches the growth media is sterile. The air supply port 202 is accessed automatically by the processor instrument 300 during the priming, inoculation and distribution stage of the cell growth process, and by the incubation instrument 400 during the incubation stage of the process. Pressurization of the growth media provides the pressure required to transport the media through the cell growth chamber 102 when the media supply valve 134 is opened.

A strain relief line or tether 204 interconnects the portable cassette's supplementary casing 112 and main casing 110. The line has a length slightly less than the lengths of the exposed media supply tube 120 and air supply line 200, so as to protect those elements from any tensile stresses brought about by an attempted movement of the two casings excessively apart from each other.

Figure 5:
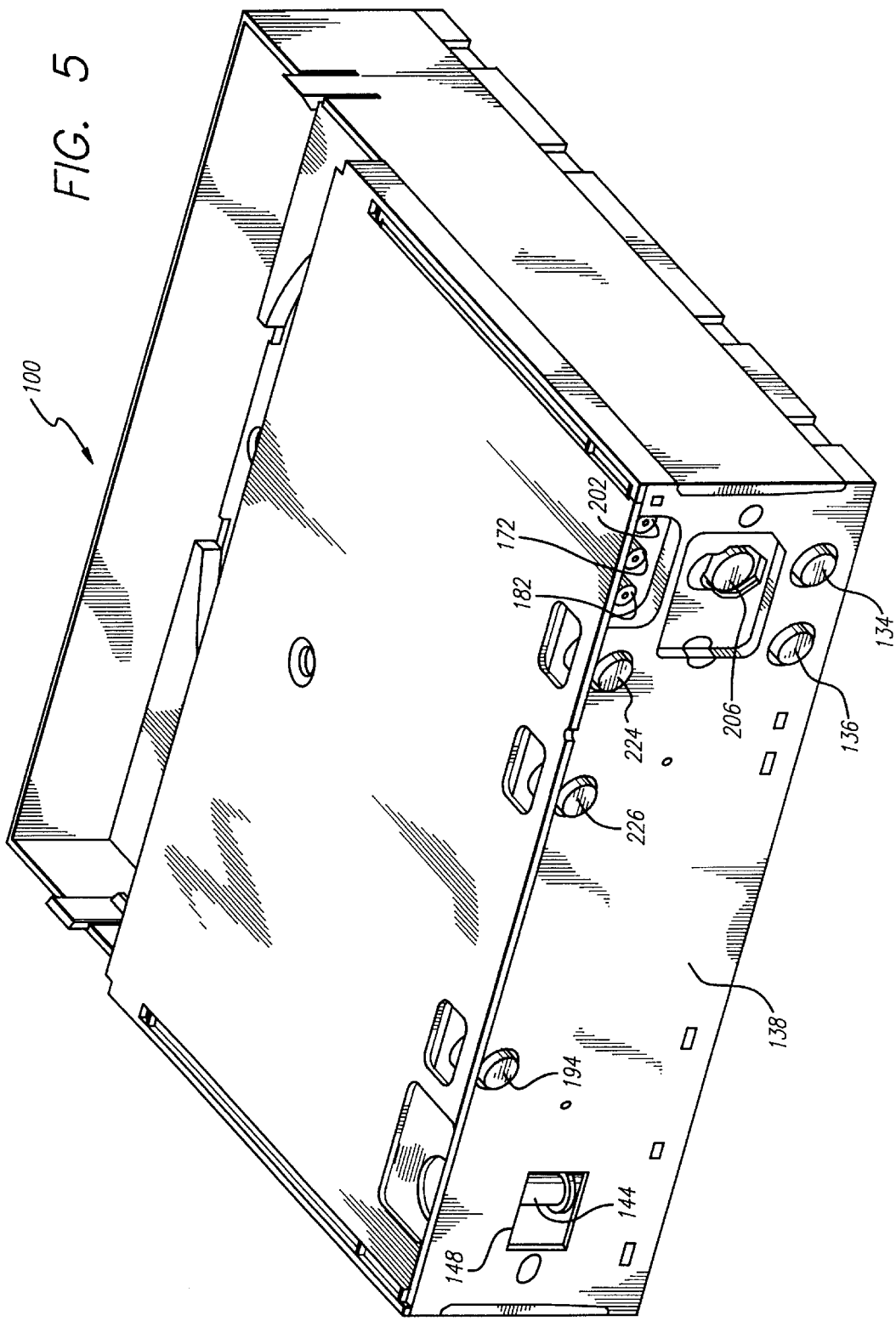
FIG. 5 is a perspective view of the rear wall of the portable cassette of FIG. 2, showing the arrangement of fluid valves that control the delivery of growth media and harvest reagents to the cassette's cell growth chamber, and further showing a drip tube used to monitor the growth media's flow rate through the chamber, and further showing the cassette's updatable memory device.

As shown specifically in FIG. 5, the portable cassette 100 further includes a non-volatile, updatable memory device, or identification key, 206 carried in a recess 208 in the cassette's rear panel 138. This memory device carries information about patient and the biological cells being grown within the cassette's cell growth chamber 102, as well as process instructions for the instrument and information about the condition of the cassette over time. The memory device is accessed automatically by both the processor instrument 300 and the incubator apparatus 400 when they receive the cassette, and the instruments retrieve the stored information and thereafter function to condition the cassette according to the retrieved information. Thus, the memory device can include detailed instructions relating to any desired program for conditioning the cassette during any particular stage of the cell growth process. Parameters such as media flow rate, gas mixture and flow rate, and temperature can be specified, and even can be made to vary over time, to effect any desired program.

In addition, the processor instrument 300 and the incubator instrument 400 are configured to update the memory device 206 with certain information about the condition of the portable cassette 100 during the time periods in which they have received and are conditioning the cassette. Examples of the kind of information to be recorded are the condition of the cassette at the occurrence of any interruption of the instrument's operation, and the timing of that interruption. This feature enables the cassette to be selectively removed from any particular instrument, as in the event of an instrument failure, and placed in a substitute instrument for a continuation of the process, as though no interruption had occurred.

One suitable memory device 206 for this purpose is available from Dallas Semiconductor, of Dallas, Tex. It has the shape of a coin, and its memory contents can be retrieved and updated merely by physically contacting any portion of the device with a special read/write device, without the need for a special electrical connector or a critical alignment of components. One example of such a read/write device is a handheld wand 502 (FIG. 1), shown as part of the system manager 500.

Figure 7:
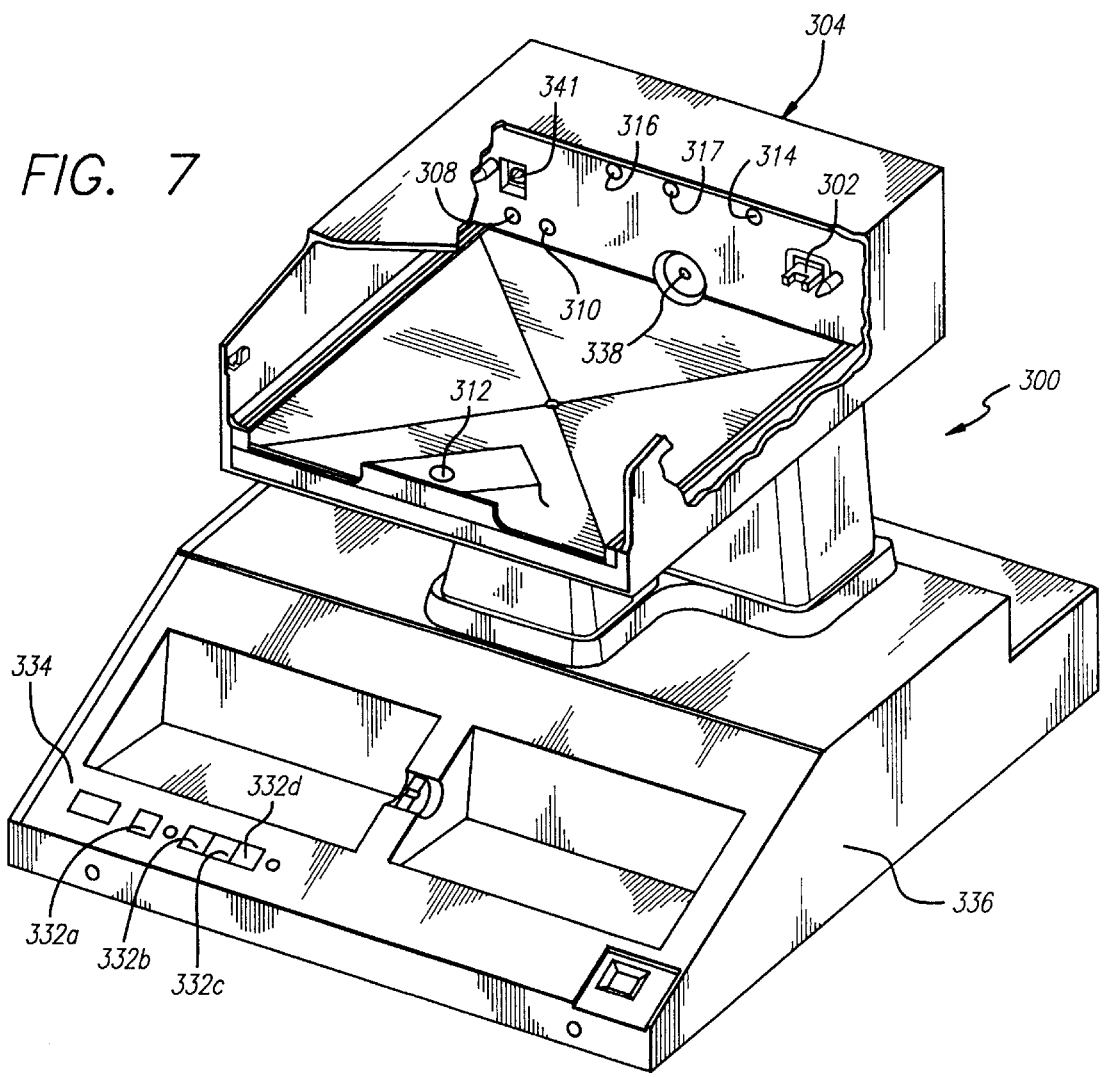
FIG. 7 is a perspective view of the processor instrument, which controls the portable cassette during both the cell inoculation and distribution stage, and the cell harvest stage, of the cell growth process.

With reference now to FIG. 7, there is shown the portion of the processor instrument 300 that receives and interfaces with the portable cassette 100 during the priming and cell inoculation and distribution stage, and later during the cell harvest stage, of the cell growth process. The processor instrument is shown to include a movable, generally rectangular platform 304 that is sized and configured to receive and support the cassette's main casing 110 and further to include an overhead shelf 306 (FIG. 1) that is sized and configured to receive and support the supplementary casing 112. Alternatively, the platform could be enlarged so as to accommodate the supplementary casing alongside the main casing, in which case the two casings need not be separable.

The processor instrument 300 further includes valve actuators 308, 310, 312 and 314, which are positioned and configured to be automatically engageable with the respective spring-biased valves 134, 136, 140 and 194 of the portable cassette 100, when the cassette's main casing 110 is properly received on the platform 304. In the preferred embodiment, the valve actuators each take the form of a simple solenoid having a plunger that can be controllably biased outwardly to engage, and release, the circular actuation plate of the associated spring-biased valve. Further, the processor instrument includes an air supply connector 315 that is configured to be automatically engageable with the cassette's air supply port 202, when the cassette's main casing is so received, and an internal valve (not shown in the drawings) that controllably supplies air through this connector to pressurize the cassette's growth media container 104.

The processor instrument 300 further includes provisions on its overhead shelf 306 for supporting two reagent bags 214 and 216 that are a part of the portable cassette 100. As shown in FIGS. 1, 2 and 7 reagents in these bags are used in the cell harvesting stage of the cell growth process, to rinse the cassette's cell growth chamber 102 and to dislodge any biological cells adhered to the cell bed 114. The reagent bags 214 and 216 are connected by tubes 218 and 220, respectively, and a common tube 222 to the cell growth chamber's enlarged center cavity 186. The tubes 218 and 220 extend through first and second reagent valves 224 and 226, respectively, which are located adjacent to the rear panel 138 of the cassette's main casing 110. These valves are identical in construction to the media supply valve 134, described above with reference to FIG. 6. The processor instrument further includes valve actuators 316 and 317 for controllably actuating the two reagent valves 224 and 226, respectively, during the cell harvesting stage of the cell growth process, as will be described below.

Figure 8:
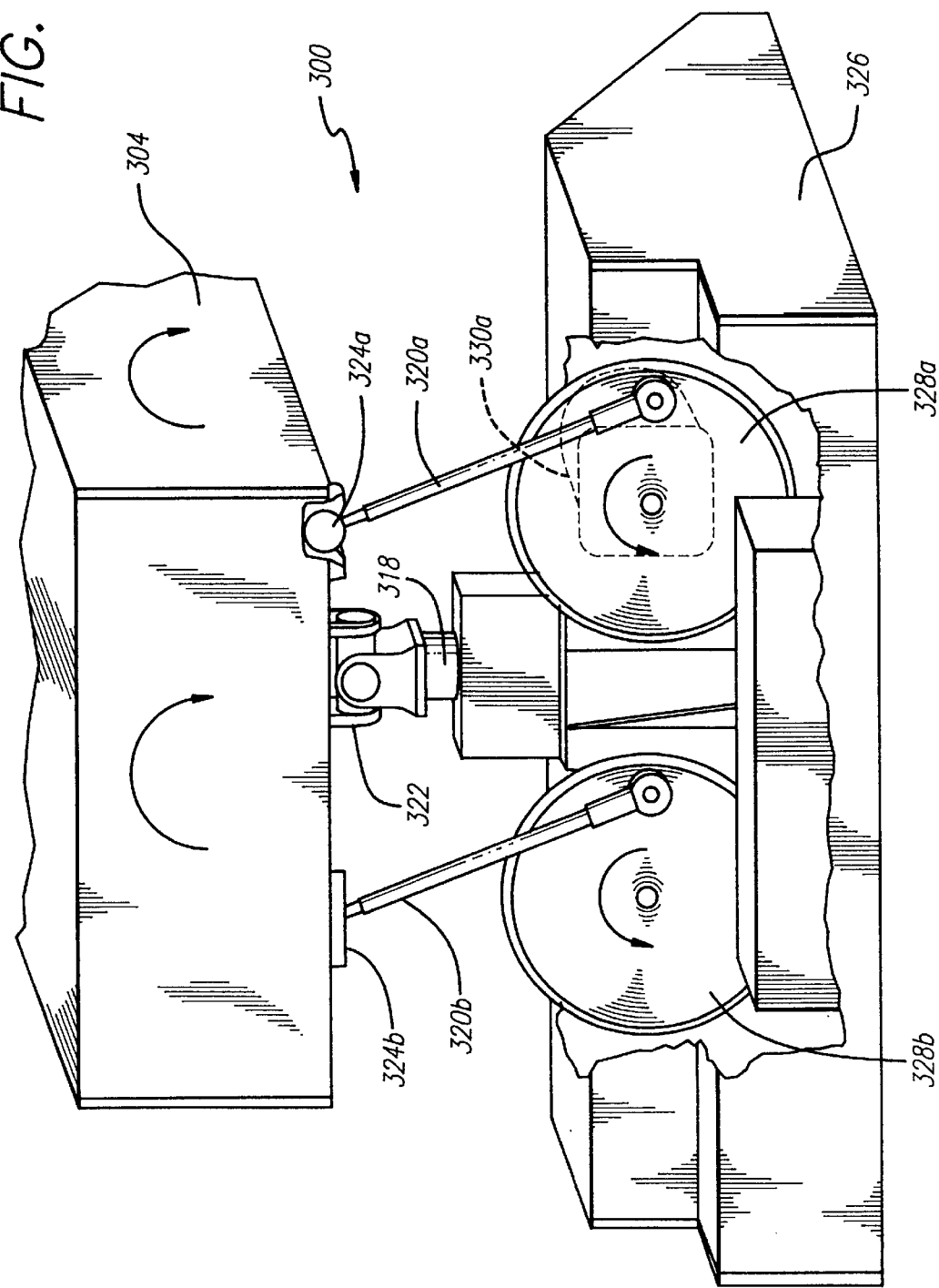
FIG. 8 is a perspective view of the base portion of the processor instrument, partially broken away, and showing the controllably rotatable wheels and legs that support the tiltable platform.

As shown in FIG. 8, the platform 304 is supported on a main support leg 318, which is located generally at the platform's center, and two auxiliary support legs 320a and 320b, which are located near the rear corners of the platform. The upper end of the main leg is secured to the platform's underside by a universal joint 322, and the upper ends of the auxiliary legs 320a and 320b are secured to the platform's underside by ball joints 324a and 324b, respectively. These joints allow limited swiveling movement of the platform. The lower end of the main leg is fixed in a base portion 326 of the processor instrument 300, while the lower ends of the auxiliary legs 320a and 320b are secured to the periphery of wheels 328a and 328b, respectively, which are mounted for controlled rotation in that base.

The wheels 328a and 328b both are controllably rotatable through 180 degrees by stepper motors 330a and 330b, respectively, to move the lower ends of the legs 320a and 320b between predetermined lower and upper limits. By independently rotating the wheels in a synchronized fashion, the platform 304, and thus the main casing 110 of the portable cassette 100, can be made to tilt in a controlled fashion. For example, positioning the wheels such that the lower ends of both auxiliary legs are at their highest positions will tilt the platform forward by a maximum amount, i.e., about 45 degrees in the preferred embodiment. Further, positioning the wheels such that the left-side auxiliary leg 320a is at its highest position and the right-side auxiliary leg 320b is at its lowest position will tilt the platform to the right by a maximum amount. By controlling the wheel positions in an appropriately synchronized fashion, the platform can be made to move in a controlled, orbital motion, which is used in the preferred embodiment to distribute the inoculated biological cells substantially uniformly in the cassette's cell growth chamber 102. The platform's HOME position is defined as the position at which it is substantially level and the lower ends of the legs are approximately at the midpoints of their vertical travel.

During the priming and cell inoculation and distribution stage of the cell growth process, the valve actuators 308, 310, 312 and 314 are conditioned to controllably release the respective valves 134, 136, 140 and 194, and the movable platform 304 is conditioned to controllably tilt, according to a predetermined operating sequence. This operating sequence, which is discussed in detail below, is selected first to prime the cell growth chamber 102 with growth media delivered from the media container 104, then to facilitate inoculation of the chamber with the biological cells to be maintained and grown, then to distribute the cells substantially uniformly throughout the chamber and thus uniformly on the planar cell bed 114, and finally to completely fill the chamber with growth media.

Table I sets forth the preferred operating sequence for the processor instrument 300 during the priming and cell inoculation and distribution stage of the cell growth process for hematopoietic progenitor cells. For each step of the sequence, the Table sets forth a brief description of the function for the step, as well as the prescribed states for the various valves 134, 136, 140 and 194 of the portable cassette 100, and for several indicators 332a, 332b and 332c on a front panel 334 of the processor instrument's base 336. The Table also sets forth, for each step of the sequence, the prescribed state for the pressurization valve that supplies pressurized air to the cassette's growth media container 104 and the prescribed position for the platform 304. The rightmost columns of the Table set forth the criteria for determining that the step has been completed, and the time threshold for sounding an alarm if each particular step has not yet been completed.

In step 1 of the operating sequence, the processor instrument 300 remains idle in its current condition while an operator places the main casing 110 of the portable cassette 100 on the platform 304, which automatically engages the air supply connector 316 of the processor instrument and positions the valves 134, 136, 140 and 194 adjacent to the respective valve actuators 308, 310, 312 and 314. Proper placement of the main casing on the platform is sensed by a microswitch 338 located on the platform. During this initial step, the operator also places the cassette's supplementary casing 112 on the overhead shelf 306 (FIG. 1) and places the media supply tube 120 that interconnects the two casings 110 and 112 in a tube sensor 340 mounted adjacent to the overhead shelf.

When the operator has completed these connections, the processor instrument 300 will illuminate the inoculate indicator 332a, the cassette-in-place indicator 332b, and the pause indicator 332c, and it will maintain closed all of the various valves of the portable cassette 100 and the processor instrument. At this time, the operator can depress the pause indicator 332c, and the operating sequence will advance to step 2. If the operator fails to depress this indicator within 300 seconds, the instrument will sound an appropriate alarm.

When it is determined that the portable cassette 100 has been properly received by the processor instrument 300, the instrument retrieves data stored in the memory device 206 that is conveniently located in the recess 208 in the rear panel 138 of the cassette's main casing 110. This data includes an identification of the particular kind of biological cells to be maintained and grown, and the processor instrument selects the appropriate operating sequence based on this retrieved data.

In step 2 of the operating sequence for hematopoietic progenitor cells of the kind to be maintained and grown in this example, the processor instrument 300 moves the platform 304 to its HOME position, in which it is substantially level. This is accomplished by moving the wheels 328a and 328b to positions where the lower ends of the two auxiliary legs 320a and 320b lie approximately midway between their extreme upper and lower positions. At this time, only the inoculate indicator 332a and the cassette-in-place indicator 332b are illuminated and all of the various valves of the portable cassette 100 and processor instrument remain closed. If the HOME position is not reached within 50 seconds, an alarm is sounded; otherwise, the operating sequence will advance to step 3.

In step 3, which is the first step of the priming sequence, the processor instrument 300 controllably tilts the platform 304 forward to an angle of about 9 degrees. This is accomplished by controllably rotating the wheels 328a and 328b so as to raise the lower ends of the auxiliary legs 320a and 320b by appropriate amounts. During this time, the conditions of the indicators 332a, 332b and 332c and of the various valves of the cassette 100 and processor instrument remain unchanged from their conditions during step 2. If the prescribed forward tilt position is not reached within 10 seconds, an alarm is sounded; otherwise, the operating sequence will advance to step 4.

In step 4, the processor instrument 300 functions to introduce growth media into the cell growth chamber 102 of the portable cassette 100, from the growth media container 104. This is accomplished by conditioning the air supply valve to open, which pressurizes the media container, and at the same time by conditioning the valve actuator 308 to controllably open the media supply valve 134, which allows the growth media to flow from the media container to the cell growth chamber via the media supply tube 120 and the media supply port 122. At this time, the inoculate indicator 332a and the cassette-in-place indicator 332b remain illuminated.

As the growth media flows into the cell growth chamber 102, displaced air is vented through a vent tube 210, which connects the harvest tube 132 (at a location upstream of the harvest valve 140) with the sterile vent 196. A Porex valve 212, which is located within this harvest tube, allows the venting air to pass through it unimpeded; however, as soon as sufficient growth media has been introduced into the chamber to reach the valve, the valve automatically closes and prevents the passage of any further material. The Porex valve is available from a company called Porex Technology, Inc. The automatic closing of the Porex valve causes an increase in the back pressure applied to the air supply pump located in the processor instrument 300, and sensing of this increased back pressure causes the operating sequence to proceed to step 5. If this back pressure increase is not sensed to have occurred within 200 seconds, an alarm is sounded.

In step 5, which is identical to step 2, the platform 304 is returned to its HOME position. If that operation is not completed within 50 seconds, an alarm is sounded. Otherwise, the program proceeds to step 6, in which excessive pressure within the cell growth chamber 102 of the portable cassette 100 is relieved by conditioning the valve actuator 314 to open the vent valve 194. This allows any excessive air to be discharged from the cell growth chamber to the sterile vent 196 and the waste container 106 via the waste reservoir 124, the waste port 126 and the waste tube 128. Completion of this step is determined to have occurred when the drip detector 302 fails to detect any drops of growth media through the drip chamber 144 for about 5 seconds. When this occurs, the operating sequence proceeds to step 7. On the other hand, if such a lack of drops has not occurred within 20 seconds, an alarm is sounded.

Step 7 requires operator involvement, for the first time since the initial placement of the portable cassette 100 on the processor instrument 300. In this step, the platform 304 remains in its HOME position, and all three indicators 332a, 332b and 332c are illuminated, with the inoculate indicator 332a being made to flash. In addition, all of the various valve actuators are conditioned to maintain their corresponding valves closed. At this time, the operator is prompted to inject a quantity of biological cells into the cell growth chamber 102 via the septum 188 located in the chamber's enlarged center cavity 186. When the operator has completed his inoculation of cells, he is prompted to depress the pause indicator 332c. In response, the processor instrument proceeds to step 8. If the operator fails to depress the pause indicator 332c within 300 seconds, an alarm is sounded.

Steps 8 through 15 all relate to the inoculation of the cell growth chamber 102 of the portable cassette 100 with the biological cells to be maintained and grown, and to the distribution of those inoculated cells substantially uniformly throughout the chamber. In all of these steps, only the inoculate indicator 332a and the cassette-in-place indicator 332b are illuminated, and all of the various valve actuators of the cassette and the processor instrument 300 are conditioned to maintain their associated valves closed.

In step 8, the processor instrument 300 tilts the platform 304, and thus the main casing 110 of the portable cassette 100, rearward to an angle of 45 degrees. When this tilt angle has been reached, the sequence advances to step 9, in which air that previously had been trapped in the enlarged center cavity 186 of the cell growth chamber 102 is allowed to migrate upwardly to the portion of the chamber that is tilted up. A bubble thereby is formed in this portion of the chamber. This step 9 has a fixed duration of 30 seconds, after which the sequence automatically proceeds to step 10.

Step 10 is identical to steps 2 and 5, discussed above, i.e., the platform 304 is conditioned to return to its HOME position. In the HOME position, the cell growth chamber 102 is substantially horizontal; however, surface tension of the growth media in the chamber prevents the bubble from migrating back to the enlarged center cavity 186. Even so, the operating sequence advances immediately to step 11 when the HOME position has been reached. If the HOME position has not been reached within 30 seconds, an alarm is sounded.

In step 11, the platform 304 is made to tilt to an angle of about 25 to 30 degrees and then to wobble in a controlled, step-wise, orbital motion. This motion moves the air bubble, which was formed in step 9, uniformly around the periphery of the cell growth chamber 102, and it thereby functions to distribute the inoculated cells throughout the chamber. This motion preferably has a cycle period of about 6 seconds, and it continues for about 120 seconds.

Steps 8–11 are substantially repeated in steps 12–15, but the wobbling occurs for a reduced time interval and at a reduced tilt angle. Step 12 tilts the platform 304 to an angle of about 45 degrees, and step 13 holds the platform in that orientation for about 30 seconds, such that a clean air bubble again forms at the edge of the cell growth chamber's periphery. Any small bubbles that broke away from the initial bubble during the wobbling of step 11 will consolidate during this step 13. Step 14 then returns the platform to its HOME position, and step 15 then tilts the platform to an angle of just 5 to 10 degrees and wobbles the platform in a controlled, step-wise, orbital motion. This causes the air bubble to circle around the cell growth chamber 102 until it eventually reaches, and is captured by, the enlarged center cavity 186. This step 15 has a duration of about 45 seconds.

Thereafter, in step 16, the air bubble that now is trapped in the enlarged center cavity 186 of the cell growth chamber 102 is purged. This is accomplished by introducing additional growth media into the chamber from the growth media container 104. In particular, the air supply valve of the processor apparatus 300 is conditioned to open, which pressurizes the media container 104. At the same time, the valve actuator 308 is conditioned to controllably open the media supply valve 134, which allows the growth media to flow from the media container to the cell growth chamber via the media supply tube 120 and the media supply port 122. Pressure relief is provided by opening the vent valve 194 in the tube 192 that connects the center cavity 186 with the drip chamber 144, which leads to the waste container 106. As soon as the drip detector 302 has detected the occurrence of drops, it is determined that the cell growth chamber has been fully purged of air. In this step, only the inoculate indicator 332a and the cassette-in-place indicator 332b are illuminated.

Thereafter, in step 17, any excess pressure in the cell growth chamber 102 is relieved by keeping open the vent valve 194, but closing the pressurization valve and the media supply valve 134. The conditions of the indicators 332a, 332b and 332c remain unchanged. This step is completed when no drips have been detected for 5 seconds. When this occurs, the priming, inoculation and cell distribution stages of the process are determined to have been completed.

Finally, in step 18, the operator is prompted to remove the portable cassette 100 from the processor instrument 300. In particular, the cassette-in-place indicator 332b is flashed, while the other two indicator 332a and 332c remain dark, and all to the various valves remain closed. The microswitch 338 detects removal of the cassette's main casing portion 110 and flashing of the indicator lamp 332b then is terminated. If the main casing is not removed within 300 seconds, an alarm is sounded.

During the time that the portable cassette 100 is received by the processor instrument 300, the occurrence of any significant events is entered as data into the memory device 206 located on the cassette's rear panel 138. This is accomplished using a read/write device 341. Examples of data that is entered include the timing of the process and the occurrence and timing of any alarms during the 18-step operating sequence.

If the 18-step operating sequence is interrupted, e.g., by the operator depressing the pause indicator 332c, at any step, the processor instrument 300 resumes implementing the sequence by proceeding through a predetermined recovery program. In particular, if the interrupt occurs during a step in which the platform 304 is to be moved to the HOME position (i.e., steps 2, 5, 10 and 14), then the instrument recovers simply by moving the platform until that HOME position has been reached. If the interrupt occurs during a step in which the platform is to undergo some other movement, the instrument recovers by first returning the platform to the HOME position and then repeating the step. On the other hand, if the interrupt occurs during a step in which the platform is not to be moved, then the instrument recovers simply by resuming the step at the time when the interrupt occurred.

During the course of the 18-step priming, inoculation, and distribution operating sequence, the contents of the memory device 206 are updated by the read/write device 341 of the processor instrument 300 to reflect such information as: 1) the inoculation start and end times, 2) the step number of the last step completed, 3) and an indication that cell inoculation and distribution has been completed. This updating ensures that, if the need ever arises, the portable cassette 100 can be transferred to a substitute processor instrument, at any step of the sequence, to complete the process.

It thus will be appreciated that the priming, cell inoculation, and cell distribution procedure is accomplished without breaking the sterile barrier of the growth media container 104, the cell growth cassette 102, and the waste container 106. Moreover, it will be appreciated that this procedure is accomplished with only minimal operator involvement, and that that minimal involvement does not require any sophisticated operator training.

After the priming, cell inoculation, and cell distribution procedure has been accomplished, and the portable cassette 100 has been removed from the processor instrument 300, the cassette is in condition for cell incubation in the incubator instrument 400. In the case of hematopoietic progenitor cells, the incubation procedure requires about two weeks. In that procedure, the cell growth chamber 102 is maintained at a temperature of about 37 degrees C., which provides optimal biological activity for a culture, and the media container 104 is maintained at a temperature of about 4 degrees C., which minimizes breakdown of heat-labile substances. At this same time, growth media is transported through the cell growth chamber, from the media container to the waste container 106, at a predetermined flow rate, and oxygen and other gases are transported through the gas chamber 118 at a predetermined flow rate. These temperature and flow rate parameters are specified by the information stored in the memory device 206 located on the cassette's rear panel 138. In general the parameters are selected to provide optimal growing conditions for the biological cells and, as mentioned above, the parameters can be made to vary with time, according to any desired program.

Figure 9:
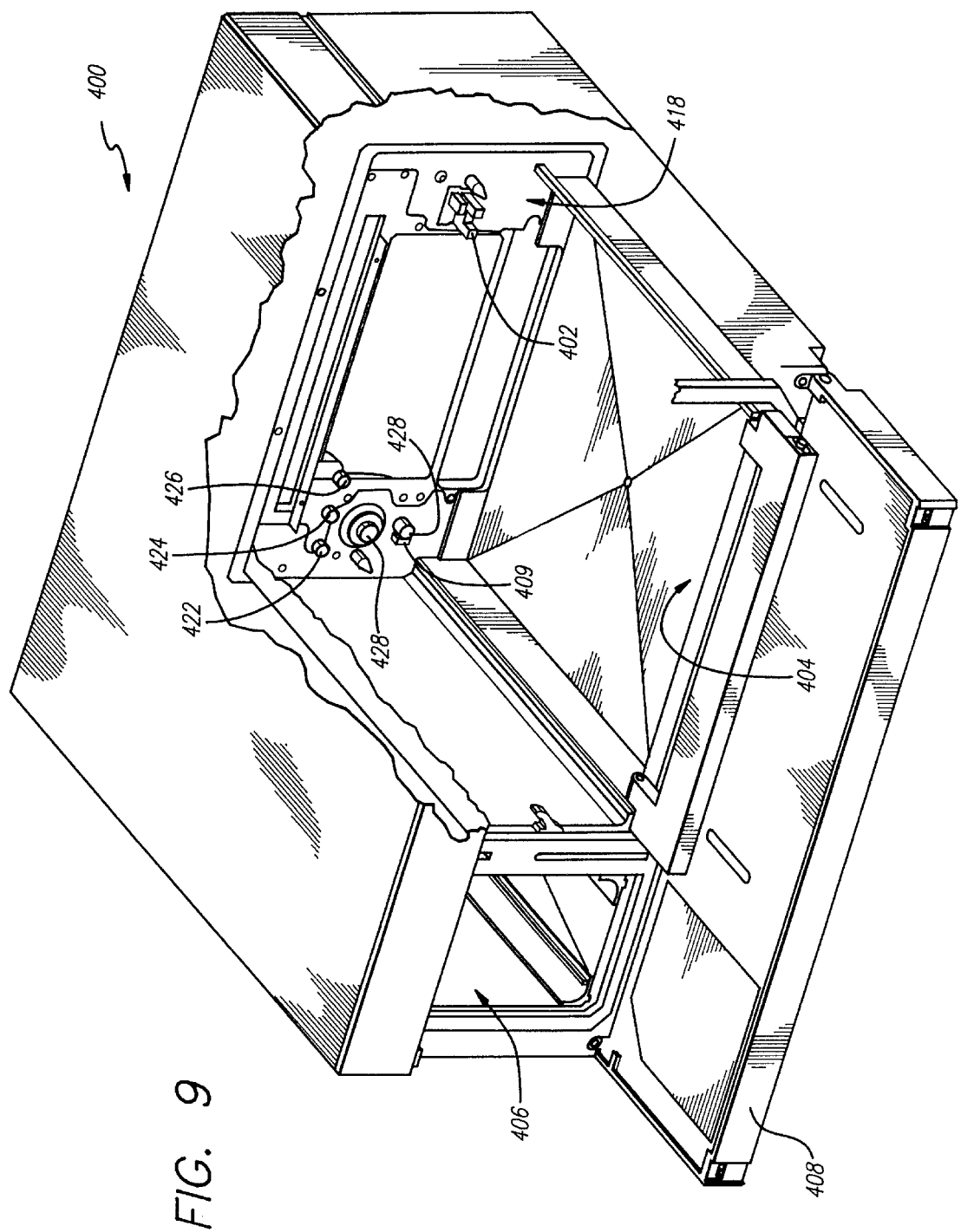
FIG. 9 is a perspective view, partially broken away, of the interface of the incubator instrument, which controls the portable cassette during the incubation stage of the cell growth process.
Figure 10:
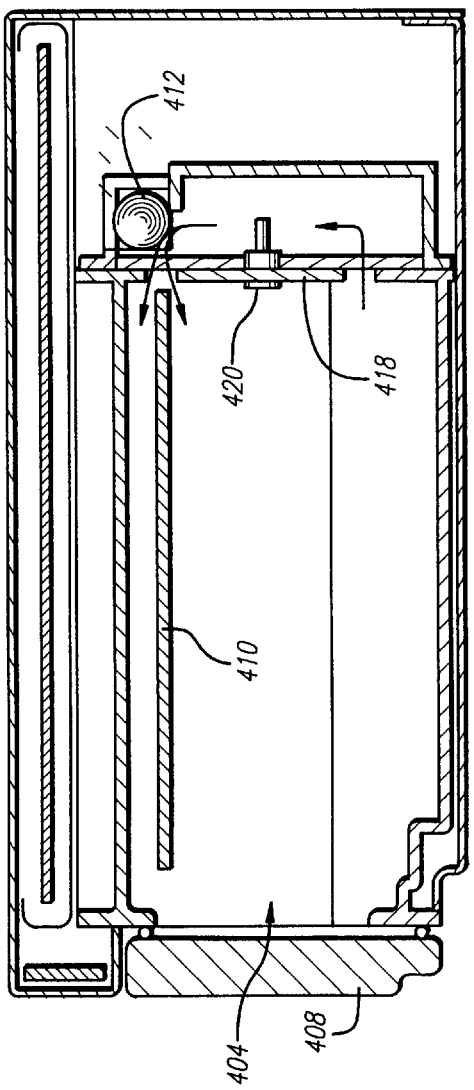
FIG. 10 is a cross-sectional view of the heating module portion of the incubator instrument of FIG. 9, which is configured to receive the main casing of the portable cassette.
Figure 11:
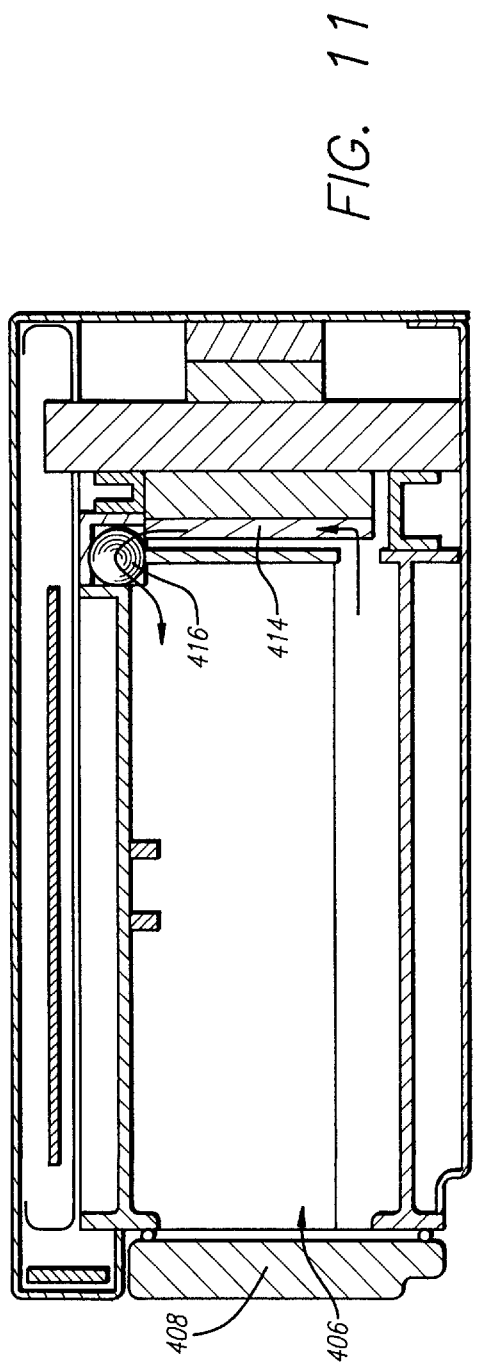
FIG. 11 is a cross-sectional view of the cooling module portion of the incubator instrument of FIG. 9, which is configured to receive the supplementary casing of the portable cassette.

More particularly, and with reference to FIGS. 9–11, the incubator instrument 400 includes two side-by-side receptacles, i.e., a first receptacle 404 sized and configured to receive the main casing 110 of the portable cassette 100, and a second receptacle 406 sized and configured to receive the cassette's supplementary casing 112. The first receptacle 404 is configured to maintain the main casing 110, and thus the cell growth chamber 102, at the prescribed 37-degree temperature, and it includes an appropriate interface to control the cassette's media supply valve 134 so as to deliver growth media at the prescribed flow rate(s) and to provide oxygen and other gases to the cassette's gas chamber 118. The second receptacle 406 is configured to maintain the supplementary casing 112, and thus the media container 104, at the prescribed 4-degree C. temperature.

The first receptacle 404 of the incubator instrument 400 is sized and configured to slidably receive the main casing 110 of the portable cassette 100. Similarly, the instrument's second receptacle 406 is sized and configured to slidably receive the cassette's supplementary casing 112. The two receptacles are arranged in a side-by-side relationship, and a sealing front door 408 that spans the two receptacles can be pivoted closed after the two casings have been inserted into their respective receptacles, to seal the receptacles from the ambient environment. A microswitch 409 detects the proper insertion of the main casing into the first receptacle.

The first receptacle 404 includes a conventional electrical heating device 410 and associated fan 412, thermostat (not shown in the drawings), and feedback control circuit (likewise, not shown), arranged in a conventional manner, for maintaining the first receptacle's interior space at its prescribed temperature. Similarly, the second receptacle 406 includes a conventional thermoelectric cooling module 414 and associated fan 416, thermostat (not shown), and feedback control circuit (not shown), for maintaining the second receptacle's interior space at its prescribed temperature.

A panel 418 at the rear of the first receptacle 404 carries a valve actuator 420 that is configured to be engageable with portable cassette's media supply valve 134, and it further carries the drip detector 402, which is configured to be engageable with the cassette's drip chamber 144. A control system regulates the flow rate of growth media through the cassette's cell growth chamber 102 by controllably actuating the valve actuator 420. The drip detector output is continuously monitored, to ensure that certain flow rate limits are not exceeded. Because the growth media does not serve as the oxygenation source for the cell culture, the flow rate can be controlled to an extremely low level, which is considered more optimal for many cell expansion applications.

An air supply connector 422 is configured to automatically mate with the cassette's air supply port 202, and pressurized air is selectively delivered to this connector from a suitable pump via an air supply valve (not shown). This selectively pressurizes the cassette's media container 104 during the incubation process. In addition, a gas supply connector 424 and a gas discharge connector 426 are positioned and configured to automatically mate with the cassette's gas-in and gas-out connections 172 and 182, respectively. This provides the desired gas mixture to the cassette's gas chamber 118 during the incubation process.

Also carried on the panel 418 at the rear of the first receptacle 404 is a read/write device 428 that can retrieve information from, and store information to, the memory device 206 carried located on the rear panel 138 of the portable cassette's main 110. When the cassette's main casing is properly inserted into the first receptacle, the read/write device retrieves the information stored in the memory device, to determine the prescribed temperature and time parameters for incubating the particular kind of cells to be grown. The incubator instrument 400 then appropriately conditions its heating and cooling control systems, described above, to maintain the prescribed temperatures, and it also then starts a timer so that visible and audible alarms can be triggered at appropriate times, as when the incubation procedure has been completed.

The read/write device 428 of the incubator instrument 400 also functions to store information to the memory device 206. This information preferably can include: 1) the incubation start and end times, 2) the occurrence and timing of any interruptions to the incubation procedure, such as alarms or power failures, 3) an identification of the amount growth media used, 4) an identification of the incubator instrument that is used, and 5) an indication that incubation is complete. This updating ensures that, if the need ever arises, the portable cassette 100 can be transferred to a substitute incubator instrument, at any step of the sequence, to complete the process.

After the incubation stage of the cell growth process has been completed, the portable cassette 100 is returned to the processor instrument 300, to harvest the cells from the cassette's cell growth chamber 102. As mentioned above, the processor instrument is configured to implement the cell harvest stage of the process by conditioning the valve actuators 312, 314, 316 and 317 to controllably release the respective harvest valve 140, center cavity valve 194, first reagent valve 224, and second reagent valve 226, and by controllably tilting the movable platform 304, according to a predetermined operating sequence. This operating sequence, which is discussed in detail below, is selected first to drain the cell growth chamber into the harvest bag 108, and then to introduce several successive reagents into the chamber from the reagent bags 214 and 216, to ensure that substantially all of the biological cells that have been grown are dislodged from the cell bed 114, each time draining the reagent and dislodged cells into the harvest bag.

Table II sets forth the preferred operating sequence for the processor instrument 300 during the cell harvest stage of the cell growth process for hematopoietic progenitor cells. For each step of the sequence, the Table sets forth a brief description of the function for the step, as well as the prescribed states for the various valves 140, 194, 224 and 226 of the portable cassette 100, and for the several indicators 332b, 332c and 332d on the front panel 334 of the processor instrument's base 326. Table II also sets forth, for each step of the sequence, the prescribed position for the platform 304. The right-most columns of Table II set forth the criteria for determining that the step has been completed and the time threshold for sounding an alarm if each particular step has not yet been completed.

In step 1 of the cell harvest operating sequence, the processor instrument 300 remains idle in its current condition while an operator places the main 110 of the portable cassette 100 on the platform 304, which automatically positions the valves 140, 194, 214 and 216 adjacent to the respective valve actuators 312, 314, 316 and 317. Proper placement of the main on the platform is sensed by the microswitch 338 located on the platform. During this initial step, the operator also attaches the two harvest reagent bags 214 and 216 to an overhead support 342, located adjacent to the instrument's overhead shelf 306. As previously mentioned, the first bag 214 contains Hank's buffered saline solution, and the second bag 216 contains is Trypsin. The operator also places the first and second reagent tubes 218 and 220 in tube sensors 344 and 346, respectively, located on the overhead support. The processor instrument 300 thereby senses that the harvesting operating sequence can be initiated.

When the operator has completed these connections, the processor instrument 300 will illuminate the cassette-in-place indicator 332b, the pause indicator 332c, and the harvest indicator 332d, and it will maintain closed all of the various valves of the portable cassette 100. At this time, the operator can depress the pause indicator 332c, and the operating sequence will advance to step 2. When that has occurred, the pause indicator 332c will darken; however, the cassette-in-place indicator 332b and the harvest indicator 332d will remain lit for the remainder of the harvesting stage. If the operator fails to depress this indicator within 300 seconds, the instrument will sound an appropriate alarm.

When it is determined that the portable cassette 100 has been properly received by the processor instrument 300, the instrument retrieves data stored in the memory device 206 that is conveniently located in the recess 208 located in the rear panel 138 of the cassette's main casing 110. This is accomplished using the read/write device 341. The retrieved data includes an identification of the particular kind of biological cells that have been grown and the appropriate procedure for harvesting those cells, and the processor instrument then selects the appropriate operating sequence based on this retrieved data. The operating sequence set forth in Table II is appropriate for harvesting hematopoietic progenitor cells.

In step 2 of the operating sequence for harvesting hematopoietic progenitor cells of the kind that have been grown in this example, the processor instrument 300 moves the is platform 304 to its HOME position, in which it is substantially level. At this time, all of the various valves of the portable cassette 100 remain closed. The cassette-in-place indicator 332b and the harvest indicator 332d remain illuminated, as they will for the entire operating sequence of the harvest stage. If the HOME position is not reached within 50 seconds, an alarm is sounded; otherwise, the operating sequence will advance to step 3.

Steps 3–8 all relate to the initial draining of fluid from the cell growth chamber 102 into the harvest bag 108. The fluid that is initially drained includes the growth media and a major portion of the biological cells that have been grown. The remaining portion of the cells remain adhered to the cell bed 114.

In step 3, the processor instrument 300 tilts its platform 304, and thus the portable cassette 100, rearward to an angle of about 45 degrees and it opens the center port valve 194, to vent the cell growth chamber 102 to the atmosphere via the vent tube 192 and the sterile vent 196. After this has been done, the process proceeds to step 4, in which the harvest valve 140 is opened. This drains most of the aforementioned fluid from the cell growth chamber into the harvest bag 108, via the harvest port 130 and the harvest tube 132. This step has a duration of 105 seconds.

Thereafter, in step 5, the platform 304 is returned to its HOME position and, in step 6, the platform is again tilted rearward to an angle of about 45 degrees. Step 7 holds the platform in this tilted position for a duration of 60 seconds, while an additional amount of the fluid is drained into the harvest bag 108. The harvest valve 140 and the center port valve 194 remain open during these steps 5–7. In step 8, the harvest valve is closed and the platform is returned to its HOME position.

Steps 9–16 all relate to the rinsing of the cell growth chamber 102 with the reagent contained in the first reagent bag 214, i.e., Hanks buffered saline solution, and the draining of the resulting rinse solution into the harvest bag 108. In step 9, the valve 224 for the first reagent is opened, and about 70 ml. of the reagent is transferred into the cell growth chamber. This represents about one half of the total amount of this reagent initially carried in the bag 214. Thereafter, in step 10, the first reagent valve 224 is closed and the center port valve 194 is opened, to vent the chamber, and the platform 304 is made to oscillate in the forward and rearward direction. This oscillation has a range of about +45 degrees to about −45 degrees, and it moves the reagent repeatedly across the cell bed 114, to dislodge a portion of the adhered cells. This motion continues for 60 seconds.

The platform 304 then returns to its HOME position, in step 11, and is made to oscillate side-to-side, in step 12. This motion again has a range of about +45 degrees to about −45 degrees and a duration of 60 seconds, and it dislodges yet further adhered cells. Thereafter, the platform returns to its HOME position, in step 13, and then tilts rearward to an angle of about 45 degrees, in step 14. The harvest valve 140 then is opened, in step 15, and the reagent and dislodged cells are thereby drained into the harvest bag 108. This step 15 has a duration of 75 seconds. Finally, in step 16, the harvest valve is closed and the platform is returned to its HOME position.

Steps 17–24 all relate to the rinsing of the cell growth chamber 102 with the reagent carried in the second reagent bag 216, i.e., Trypsin, and the draining of the resulting rinse solution into the harvest bag 108. Trypsin is a protein that is effective in dislodging nearly all of the remaining cells adhered to the cell bed 114. The steps 17–24 are identical to steps 9–16, discussed above, except that step 17 opens the valve 226 for the second reagent, which contrasts with step 9's opening of the valve 216 for the first reagent. After the final step, i.e., step 24, the platform 304 is in its HOME position.

Steps 25–32 all relate to a second rinsing of the cell growth chamber 102 with the reagent (Hank's buffered saline solution) carried in the first reagent bag 214. These steps are identical to steps 9–16, discussed above, and they serve to transfer to the harvest bag 108 most of any the cells remaining in the chamber. After step 32, the platform 304 is in its HOME position.

Finally, in step 33, all of the valves of the portable cassette 100 and the processor instrument 300 are closed and the cassette-in-place indicator 332b is made to flash. In addition, an audible prompt is provided, to prompt the operator to remove the cassette from the instrument and to extract the harvest bag 108. At this time, the harvest bag should carry substantially all of the biological cells present in the cell growth chamber 102 when the harvesting procedure was initiated, as well as the growth media then present in the chamber, about 140 ml. of Hank's buffered saline solution, and about 70 ml. of Trypsin.

If the 33-step operating sequence of the harvesting procedure is interrupted at any step, e.g., by the operator depressing the pause indicator 332c, the processor instrument 300 resumes implementing the sequence by proceeding through a predetermined recovery program. In particular, if the interrupt occurs during a step in which the platform 304 is to be moved to the HOME position (i.e., steps 2, 5, 8, 11, 13, 16, 19, 21, 24, 27, 29 and 32), then the instrument recovers simply by moving the platform until that HOME position has been reached. If the interrupt occurs during a step in which the platform is to undergo some other movement, the instrument recovers by first returning the platform to the HOME position and then repeating the step. On the other hand, if the interrupt occurs during a step in which the platform is not to be moved, then the instrument recovers simply by resuming the step at the time when the interrupt occurred.

While the portable cassette 100 is received by the processor instrument 300, the occurrence of any significant events is entered as data by the read/write device 341 into the memory device 206 located on the cassette's rear panel 138. Examples of such data include: 1) the harvest start and end times, 2) an identification of the last operating step completed, 3) the occurrence and timing of any alarms during its 33-step operating sequence, and 4) an indication that cell harvesting has been completed. This updating ensures that, if the need ever arises, the portable cassette 100 can be transferred to a substitute processor instrument, at any step of the sequence, to complete the process.

It thus will be appreciated that the cell harvesting procedure is accomplished without breaking the sterile barrier of the cell growth cassette 102 and the harvest bag 108. Moreover, it will be appreciated that this procedure is accomplished with only minimal operator involvement, and that that minimal involvement does not require any sophisticated operator training.

As mentioned above, the system manager 500 (FIG. 1) provides an operator interface and monitors the cell growth occurring simultaneously in as many as 50 separate portable cassettes 100. The system manager is networked to a plurality of processor instruments 300 and a plurality of incubator instruments 400, to monitor the status of those instruments and any portable cassettes they might at any time be processing. No direct control of those instruments by the system manager occurs; rather, the system manager's only function in this regard is to monitor the instruments and to amass information pertinent to the condition of each of the cassettes during the course of its cell growth.

Examples of the kind of information that the system manager 500 can receive from any particular processor instrument 300 include: 1) the instrument's status and the particular step number it might currently be implementing, 2) the settings of the valves of the portable cassette 100 being processed, 3) the readings of the instrument's various sensors, 4) the information stored in the memory device 206 of the associated portable cassette, 5) the status of any alarms, and 6) an identification of the particular operating sequence being implemented. Examples of the kind of information that the system manager can receive from any particular incubator instrument 400 include: 1) the instrument's status and its control settings, 2) the readings of the instrument's various sensors, 3) the information stored in the memory device 206 of the associated portable cassette, 4) the status of any alarms, and 5) an identification of the particular operating sequence being implemented. A printer 503 can print this information at the end of the cell growth process, or on command, to provide a written record of the process, for archival purposes.

Another function of the system manager 500 is to initially load pertinent information into the memory device 206 associated with each portable cassette 100, before the cell growth process is begun. Such information can include: 1) an identification of the particular patient for whom the cells are to be grown, 2) an identification of the type of cells to be grown, 3) an identification of the particular portable cassette being used and the particular lots of growth media and harvest reagents being used, 4) a real time and date stamp, and 5) an identification of any particular processing parameters (e.g., incubation temperature and duration) for the cell growth process. To this end, the system manager includes a keyboard 504 for manual data entry and a bar code reader 506 for scanning bar code labels on reagent bags and the like. The system manager also includes the read/write device 502, for loading the information into the memory device.

The system manager 500 also can be used to check the memory device 206 after incubation, but before cell harvesting. This check can ensure that the portable cassette 100 is, in fact, ready to undergo the cell harvesting procedure.

It should be appreciated from the foregoing description that the present invention provides an apparatus, and related method, that receives, maintains and grows biological cells ex vivo within a portable cassette, without exposing the cells to the external environment. The portable cassette is used in combination with a processor instrument that inoculates the cassette with cells of the kind to be grown and distributes those cells in a predetermined pattern (e.g., uniformly) throughout a cell growth chamber, and thereafter in combination with an incubator instrument that incubates the cell growth chamber so that the cells are optimally expanded. The same processor instrument then is used to harvest the expanded cells from the portable cassette. Both instruments are configured to condition the portable cassette during stages of the cell growth process, without disturbing the cassette's sterile system. In addition an updatable memory device associated with the cassette stores significant information about the cassette and its condition during the various steps of the cell growth process. Such information is useful both for subsequent archival purposes and for facilitating a resumption of the cell growth process in the event of any instrument failure or significant alarm condition.

Although the invention has been described in detail with reference only to the presently preferred embodiment, those skilled in the art will appreciate that various modifications can be made without departing from the invention. Accordingly, the invention is defined only by the following claims.

TABLE I

Processor Sequencing Chart - Inoculate Procedure

| Step | Description | Inoculate Indicator | Cassette-in-place Indicator | Pause Indicator | B-Media Supply | C-Waste | D-Harvest Bag | E-Center Port |
|---|---|---|---|---|---|---|---|---|
|  | [Idle to Run transition, self-tests] |  |  |  |  |  |  |  |
| 1 | Programmed pause for container set up | Lit | Lit | Lit | C | C | C | C |
| 2 | Go to home | Lit | Lit | Dark | C | C | C | C |
| 3 | Tilt cassette to prime angle | Lit | Lit | Dark | C | C | C | C |
| 4 | Fill cassette w/liquid | Lit | Lit | Dark | ▓ | C | C | C |
| 5 | Go to home | Lit | Lit | Dark | C | C | C | C |
| 6 | Relieve excess cell bed pressure | Lit | Lit | Dark | C | ▓ | C | C |
| 7 | Programmed pause for innoculum addition | Flash | Lit | Lit | C | C | C | C |
| 8 | Tilt cassette to +45° | Lit | Lit | Dark | C | C | C | C |
| 9 | Wait for Bubble to form | Lit | Lit | Dark | C | C | C | C |
| 10 | Go to Home | Lit | Lit | Dark | C | C | C | C |
| 11 | Wobbulate to distribute cells | Lit | Lit | Dark | C | C | C | C |
| 12 | Tilt cassette to +45° | Lit | Lit | Dark | C | C | C | C |
| 13 | Wait for Bubble to form | Lit | Lit | Dark | C | C | C | C |
| 14 | Go to Home | Lit | Lit | Dark | C | C | C | C |
| 15 | Wobbulate to center bubble | Lit | Lit | Dark | C | C | C | C |
| 16 | Purge center port | Lit | Lit | Dark | ▓ | C | C | ▓ |
| 17 | Relieve cell bed pressure | Lit | Lit | Dark | C | C | C | ▓ |
| 18 | Remove cell cassette for incubation<br>▓ [Return to Idle State] | Dark | Flash | Dark | C | C | C | C |

TABLE I-continued

Processor Sequencing Chart - Inoculate Procedure

| Step | Description | F-Harvest Reag. #1 | G-Harvest Reag. #2 | Pressurization Valve | Completion Criteria | Alarm Checks Step Done Timeout (seconds) | Motion Timeout (seconds) |
|---|---|---|---|---|---|---|---|
| | [Idle to Run transition, self-tests] | | | | | | |
| 1 | Programmed pause for container set up | C | C | C | Key Press | 300 (alert) | — |
| 2 | Go to home | C | C | C | Program Done | 50 | — |
| 3 | Tilt cassette to prime angle | C | C | C | Program Done | 10 | — |
| 4 | Fill cassette w/liquid | C | C | O (alert) | Pressure Rise to 5 | 300 (alert) | — |
| 5 | Go to home | C | C | C | Program Done | 50 | — |
| 6 | Relieve excess cell bed pressure | C | C | C | No Drips for 5 sec | 20 (alert) | — |
| 7 | Programmed pause for innoculum addition | C | C | C | Key press | 300 (alert) | — |
| 8 | Tilt cassette to +45° | C | C | C | Program Done | 10 | — |
| 9 | Wait for Bubble to form | C | C | C | 30 seconds | — | — |
| 10 | Go to Home | C | C | C | Program Done | 50 | — |
| 11 | Wobbulate to distribute cells | C | C | C | Program Done | 180 | 10 |
| 12 | Tilt cassette to +45° | C | C | C | Program Done | 10 | — |
| 13 | Wait for Bubble to form | C | C | C | 30 seconds | — | — |
| 14 | Go to Home | C | C | C | Program Done | 50 | — |
| 15 | Wobbulate to center bubble | C | C | C | Program Done | 45 | 10 |
| 16 | Purge center port | C | C | O (alert) | Drip detection | 10 (alert) | — |
| 17 | Relieve cell bed pressure | C | C | C | No drips for 5 sec | 20 (alert) | — |
| 18 | Remove cell cassette for incubation | C | C | C | DBC Microswitch open | 300 (alert) | — |
| (shaded) | [Return to Idle State] | | | | | | |

C = Valve closed (Off)
O = Valve open (On) - Shaded
For alarm columns: shaded entry = alert, non-shaded entry = alarm

TABLE II

Processor Sequencing Chart - Harvest Procedure

| Step | Description | Harvest Indicator | Cassette-in-place Indicator | Pause Indicator | B-Media Supply | C-Waste | D-Harvest Bag | E-Center Port | F-Harvest Reag. #1 |
|---|---|---|---|---|---|---|---|---|---|
| | [Idle to Run transition, self-test] | | | | | | | | |
| 1 | Programmed pause for bag set up | Lit | Lit | Lit | C | C | C | C | C |
| 2 | Go to home | Lit | Lit | Dark | C | C | C | C | C |
| 3 | Tilt Cassette to +45 | Lit | Lit | Dark | C | C | C | O | C |
| 4 | Drain cell bed into harvest bag | Lit | Lit | Dark | C | C | O | O | C |
| 5 | Go to home | Lit | Lit | Dark | C | C | O | O | C |
| 6 | Tilt Cassette to +45 | Lit | Lit | Dark | C | C | O | O | C |
| 7 | Drain cell bed into harvest bag | Lit | Lit | Dark | C | C | O | O | C |
| 8 | Go to home | Lit | Lit | Dark | C | C | C | O | C |
| 9 | Add 70 ml of Reagent #1 to cell bed | Lit | Lit | Dark | C | C | C | C | O |
| 10 | X axis wash | Lit | Lit | Dark | C | C | C | O | C |
| 11 | Go to home | Lit | Lit | Dark | C | C | C | O | C |
| 12 | Y axis wash | Lit | Lit | Dark | C | C | C | O | C |
| 13 | Go to home | Lit | Lit | Dark | C | C | C | O | C |
| 14 | Tilt Cassette to +45 | Lit | Lit | Dark | C | C | C | O | C |
| 15 | Drain cell bed into harvest bag | Lit | Lit | Dark | C | C | O | O | C |
| 16 | Go to home | Lit | Lit | Dark | C | C | C | O | C |
| 17 | Add Reagent #2 to cell bed | Lit | Lit | Dark | C | C | C | C | C |

TABLE II-continued

Processor Sequencing Chart - Harvest Procedure

| | | | | | | | | | |
|---|---|---|---|---|---|---|---|---|---|
| 18 | X axis wash | Lit | Lit | Dark | C | C | C | ▓ | C |
| 19 | Go to home | Lit | Lit | Dark | C | C | C | ▓ | C |
| 20 | Y axis wash | Lit | Lit | Dark | C | C | C | ▓ | C |
| 21 | Go to home | Lit | Lit | Dark | C | C | C | ▓ | C |
| 22 | Tilt Cassette to +45 | Lit | Lit | Dark | C | C | C | ▓ | C |
| 23 | Drain cell bed into harvest bag | Lit | Lit | Dark | C | C | ▓ | ▓ | C |
| 24 | Go to home | Lit | Lit | Dark | C | C | C | ▓ | C |
| 25 | Add rest of Reagent #1 to cell bed | Lit | Lit | Dark | C | C | C | C | ▓ |
| 26 | X axis wash | Lit | Lit | Dark | C | C | C | ▓ | C |
| 27 | Go to home | Lit | Lit | Dark | C | C | C | ▓ | C |
| 28 | Y axis wash | Lit | Lit | Dark | C | C | C | ▓ | C |
| 29 | Go to home | Lit | Lit | Dark | C | C | C | ▓ | C |
| 30 | Tilt Cassette to +45 | Lit | Lit | Dark | C | C | C | ▓ | C |
| 31 | Drain cell bed into harvest bag | Lit | Lit | Dark | C | C | ▓ | ▓ | C |
| 32 | Go to home | Lit | Lit | Dark | C | C | C | ▓ | C |
| 33 | Recover Harvest Bag, Remove cassette [Return to Idle State] | Dark | Flash | Dark | C | C | C | C | C |

| Step | Description | G-Harvest Reag. #2 | Power Failure/Pause Recovery | Completion Criteria | Step Done Timeout (seconds) | Motion Timeout (seconds) |
|---|---|---|---|---|---|---|
| | [Idle to Run transition, self-tests] | | | | | |
| 1 | Programmed pause for bag set up | C | Resume exactly where left off | Key Press | ▓ | — |
| 2 | Go to home | C | Sequence 7 | Program Done | 50 | — |
| 3 | Tilt Cassette to +45 | C | Sequence 7, Repeat Step | Program Done | 10 | — |
| 4 | Drain cell bed into harvest bag | C | Resume exactly where left off | 105 seconds | — | — |
| 5 | Go to home | C | Sequence 7 | Program Done | 50 | — |
| 6 | Tilt Cassette to +45 | C | Sequence 7, Repeat Step | Program Done | 10 | — |
| 7 | Drain cell bed into harvest bag | C | Resume exactly where left off | 60 seconds | — | — |
| 8 | Go to home | C | Sequence 7 | Program Done | 50 | — |
| 9 | Add 70 ml of Reagent #1 to cell bed | C | Resume exactly where left off | 22 seconds | — | — |
| 10 | X axis wash | C | Sequence 7, Resume at time left | 60 seconds* | — | 10 |
| 11 | Go to home | C | Sequence 7 | Program Done | 50 | — |
| 12 | Y axis wash | C | Sequence 7, Resume at time left | 60 seconds* | — | 10 |
| 13 | Go to home | C | Sequence 7 | Program done | 50 | — |
| 14 | Tilt Cassette to +45 | C | Sequence 7, Repeat Step | Program done | 10 | — |
| 15 | Drain cell bed into harvest bag | C | Resume exactly where left off | 75 seconds | — | — |
| 16 | Go to home | C | Sequence 7 | Program Done | 50 | — |
| 17 | Add Reagent #2 to cell bed | ▓ | Resume exactly where left off | 40 seconds | — | — |
| 18 | X axis wash | C | Sequence 7, Resume at time left | 60 seconds* | — | 10 |
| 19 | Go to home | C | Sequence 7 | Program Done | 50 | — |
| 20 | Y axis wash | C | Sequence 7, Resume at time left | 60 seconds* | — | 10 |
| 21 | Go to home | C | Sequence 7 | Program done | 50 | — |
| 22 | Tilt Cassette to +45 | C | Sequence 7, Repeat Step | Program done | 10 | — |
| 23 | Drain cell bed into harvest bag | C | Resume exactly where left off | 75 seconds | — | — |
| 24 | Go to home | C | Sequence 7 | Program Done | 50 | — |
| 25 | Add rest of Reagent #1 to cell bed | C | Resume exactly where left off | 40 seconds | — | — |
| 26 | X axis wash | C | Sequence 7, Resume at time left | 60 seconds* | — | 10 |
| 27 | Go to home | C | Sequence 7 | Program Done | 50 | — |
| 28 | Y axis wash | C | Sequence 7, Resume at time left | 60 seconds* | — | 10 |
| 29 | Go to home | C | Sequence 7 | Program done | 50 | — |
| 30 | Tilt Cassette to +45 | C | Sequence 7, Repeat Step | Program done | 10 | — |
| 31 | Drain cell bed into harvest bag | C | Resume exactly where left off | 90 seconds | — | — |
| 32 | Go to home | C | Sequence 7 | Program Done | 50 | — |

TABLE II-continued

Processor Sequencing Chart - Harvest Procedure

| 33 | Recover Harvest Bag, Remove cassette [Return to Idle State] | C | Resume exactly where left off | Microswitch Open | | — |

C = Valve closed (Off)
O = Valve open (On) - Shaded

We claim:

1. A processor apparatus for use in combination with a portable, self-contained cell growth cassette, separate from the processor apparatus and configured to receive, maintain and grow biological cells ex vivo, wherein the portable cassette includes a cell growth chamber configured to carry a quantity of biological cells and growth media and further includes a media flow path communicating with the cell growth chamber, the cell growth chamber and the media flow path being part of a sterilizable system that is closed to the external environment, and wherein the processor apparatus functions to prime the cell growth chamber with a growth medium and to distribute the biological cells within the cell growth chamber, the processor apparatus comprising:

a support configured to removably receive, and mechanically couple to, the portable cassette, and further configured to be movable in a controlled manner;

a flow control actuator mechanically engageable with the media flow path of the portable cassette when the cassette is received by, and mechanically coupled to, the support; and a controller that controls the flow control actuator, such that the flow control actuator causes a quantity of the growth medium to be controllably transported via the media flow path to the cell growth chamber of the portable cassette, and that controllably moves the support, and thereby the portable cassette, in a predetermined manner, such that the biological cells are distributed throughout the cell growth chamber, without operator intervention and without exposing the closed, sterilizable system to the external environment.

2. A processor apparatus as defined in claim 1, wherein:

the portable cassette further includes a flow control device engageable with the media flow path; and the flow control actuator is engageable with the flow control device of the portable cassette when the cassette is received by, and mechanically coupled to, the support, to control the transport of growth media via the media flow path to the cell growth chamber.

3. A processor apparatus as defined in claim 2, wherein:

the controller includes a media flow sensor that senses the transport of a determined quantity of growth media via the media flow path to the cell growth chamber of the portable cassette and that generates a corresponding detection signal; and the controller is configured to control the flow control actuator so as to terminate the transport of growth media via the media flow path to the cell growth chamber when a detection signal has been generated by the media flow sensor.

4. A processor apparatus as defined in claim 2, wherein the controller is configured to control the flow control actuator so as to terminate the transport of growth media via the media flow path to the cell growth chamber when a predetermined time period has elapsed.

5. A processor apparatus as defined in claim 1, wherein:

the controller includes a media flow sensor that senses the transport of a determined quantity of growth media via the media flow path to the cell growth chamber of the portable cassette and that generates a corresponding detection signal; and the controller is configured to control the flow control actuator so as to terminate the transport of growth media via the media flow path to the cell growth chamber when a detection signal has been generated by the media flow sensor.

6. A processor apparatus as defined in claim 1, wherein:

the controller is configured to control the flow control actuator such that a determined quantity of growth media is transported via the media flow to the cell growth chamber of the portable cassette and a gas bubble remains within the cell growth chamber;

the portable cassette further includes an inoculation port through which a quantity of biological cells to be maintained and grown within the cell growth chamber of the cassette can be delivered; and the controller is configured to controllably move the support such that the gas bubble moves within the cell growth chamber of the portable cassette in a predetermined manner, to mix the biological cells substantially uniformly with the growth media within the growth chamber.

7. A processor apparatus as defined in claim 6, wherein the controller is further configured to control the flow control actuator, after the moving of the support has mixed the biological cells with the growth media, such that sufficient additional growth media is transported via the media flow path to the cell growth chamber, to substantially displace the gas bubble.

8. A processor apparatus as defined in claim 1, wherein:

the cell growth chamber of the portable cassette further includes a harvest port; and the controller is configured to discharge biological cells and growth media from the cell growth chamber of the portable cassette to a harvest container, via the harvest port, without operator intervention and without exposing the closed, sterilizable system to the external environment.

9. A processor apparatus as defined in claim 1, wherein:

the cell growth chamber of the portable cassette includes a media inlet port, a media outlet port, a cell inoculation port, and a harvest port;

the portable cassette further includes a media container that carries a predetermined quantity of the growth medium, for delivery to the cell growth chamber via the media inlet port, a waste container for carrying media discharged from the growth chamber via the media outlet port, and a harvest container for carrying biological cells and growth media discharged from the growth chamber via the harvest port;

the cell growth chamber, the media container, the waste container, and the harvest container of the portable cassette form a closed, sterilizable system that is configured to maintain the biological cells and the growth media without exposure to the external environment; and the processor apparatus is configured to prime the cell growth chamber with growth media and to harvest biological cells from the cell growth chamber without operator intervention and without exposing, the portable cassette's closed, sterilizable system to the external environment.

10. A processor apparatus as defined in claim 1, wherein:

the portable cassette further includes a casing that encases the cell growth chamber and at least a portion of the media flow path;

the portable cassette further includes a memory device carrying information about the cell growth chamber and the biological cells and growth media it carries and information about the condition of the cell growth chamber over time; and the processor apparatus further includes a device that operates, when the casing is received by the support, and mechanically coupled thereto, to retrieve information from the memory device of the portable cassette.

11. A processor apparatus as defined in claim 1, wherein:

the portable cassette further includes a casing that encases the cell growth chamber and at least a portion of the media flow path;

the portable cassette further includes a memory device carrying information about the cell growth chamber and the biological cells and growth media it carries, including processing parameter instructions; and the processor apparatus further includes a device that operates, when the casing is received by the support, and mechanically coupled thereto, to retrieve processor parameter instructions from the memory device of the portable cassette, the apparatus thereafter operating according to the retrieved instructions.

12. A processor apparatus as defined in claim 1, wherein:

the portable cassette further includes a casing that encases the cell growth chamber and at least a portion of the media flow path;

the portable cassette further includes an updatable memory device carrying information about the condition of the cell growth chamber over time; and the processor apparatus further includes a device that operates, when the casing is received by the support, and mechanically coupled thereto, to record information in the memory device of the portable cassette, including information relating to the priming of the cell growth chamber with a growth medium, the inoculation of the chamber with biological cells, or the distribution of cells within the chamber.

13. A processor apparatus as defined in claim 1, wherein:

the cell growth chamber of the portable cassette includes at least one generally planar cell bed; and the support is configured to be controllably tiltable about two horizontal axes, such that fluid in the cell growth chamber is distributed substantially uniformly.

* * * * *